US007111938B2

(12) United States Patent
Andino et al.

(10) Patent No.: US 7,111,938 B2
(45) Date of Patent: Sep. 26, 2006

(54) AUTOMATIC LENS DESIGN AND MANUFACTURING SYSTEM

(75) Inventors: Rafael Victor Andino, Lawrenceville, GA (US); Courtney Flem Morgan, Alpharetta, GA (US); Joseph Michael Lindacher, Lawrenceville, GA (US)

(73) Assignee: Novartis AG, Basel (CH)

( * ) Notice: Subject to any disclaimer, the term of this patent is extended or adjusted under 35 U.S.C. 154(b) by 83 days.

(21) Appl. No.: 10/476,030

(22) PCT Filed: Apr. 26, 2002

(86) PCT No.: PCT/EP02/04649

§ 371 (c)(1),
(2), (4) Date: Jul. 7, 2004

(87) PCT Pub. No.: WO02/088830

PCT Pub. Date: Nov. 7, 2002

(65) Prior Publication Data

US 2004/0246440 A1    Dec. 9, 2004

Related U.S. Application Data

(60) Provisional application No. 60/313,898, filed on Aug. 21, 2001, provisional application No. 60/287,189, filed on Apr. 27, 2001.

(51) Int. Cl.
*A61B 3/10* (2006.01)

(52) U.S. Cl. .................................................. 351/212

(58) Field of Classification Search ................ 351/177, 351/178, 205, 212, 219, 221, 247
See application file for complete search history.

(56) References Cited

U.S. PATENT DOCUMENTS

| 4,614,413 A | 9/1986 | Obssuth ...................... 351/161 |
| 4,702,573 A | 10/1987 | Morstad ..................... 351/161 |
| 4,859,049 A | 8/1989 | Muller ....................... 351/161 |
| 4,874,234 A | 10/1989 | Wichterle .................. 351/161 |

(Continued)

FOREIGN PATENT DOCUMENTS

EP        0 806 694        11/1997

(Continued)

*Primary Examiner*—George Manuel
(74) *Attorney, Agent, or Firm*—Jian Zhou

(57) ABSTRACT

The present invention provides a method for designing and making a customized ophthalmic lens, such as a contact lens or an intraocular lens, capable of correcting high-order aberrations of an eye. The posterior surface of the customized contact lens is designed to accommodate the corneal topography of an eye. The design of the customized ophthalmic lens is evaluated and optimized in an optimizing routine using a computational model eye that reproduces the aberrations and corneal topography of an eye. The present invention also provides a system and method for characterizing the optical metrology of a customized ophthalmic lens that is designed to correct aberrations of an eye. Furthermore, the present invention provides a business model and method for placing an order for a pair of customized ophthalmic lenses.

35 Claims, 8 Drawing Sheets

U.S. PATENT DOCUMENTS

| | | | |
|---|---|---|---|
| 4,878,750 A | 11/1989 | Sekiguchi | 351/212 |
| 5,019,098 A | 5/1991 | Mercier | 623/6 |
| 5,050,981 A | 9/1991 | Roffman | 351/177 |
| 5,071,244 A | 12/1991 | Ross | 351/161 |
| 5,191,366 A | 3/1993 | Kashiwagi | 351/177 |
| 5,204,703 A | 4/1993 | Hutchinson et al. | 351/210 |
| 5,220,359 A | 6/1993 | Roffman | 351/177 |
| 5,341,604 A | 8/1994 | Wood | 51/165 |
| 5,404,183 A | 4/1995 | Seidner | 351/161 |
| 5,493,350 A | 2/1996 | Seidner | 351/161 |
| 5,499,064 A | 3/1996 | Vansaghi | 351/158 |
| 5,526,071 A | 6/1996 | Seidner et al. | 351/161 |
| 5,619,289 A | 4/1997 | Seidner et al. | 351/161 |
| 5,635,998 A | 6/1997 | Baugh | 351/161 |
| 5,677,750 A | 10/1997 | Qi | 351/205 |
| 5,691,797 A | 11/1997 | Seidner et al. | 351/161 |
| 5,777,719 A | 7/1998 | Williams et al. | 351/212 |
| 5,861,114 A | 1/1999 | Roffman et al. | 264/2.5 |
| 5,888,122 A | 3/1999 | Gupta et al. | 451/42 |
| 5,949,521 A | 9/1999 | Williams et al. | 351/246 |
| 5,963,300 A | 10/1999 | Horwitz | 351/209 |
| 5,971,542 A | 10/1999 | Volker et al. | 351/161 |
| 6,082,856 A | 7/2000 | Dunn et al. | 351/160 |
| 6,086,204 A | 7/2000 | Magnante | 351/212 |
| 6,089,711 A | 7/2000 | Blackenbecler et al. | 351/160 |
| 6,095,651 A | 8/2000 | Williams et al. | 351/246 |
| 6,109,749 A | 8/2000 | Bernstein | 351/161 |
| 6,122,999 A | 9/2000 | Durazo et al. | 82/1.11 |
| 6,176,578 B1 | 1/2001 | Clutterbuck et al. | 351/160 |
| 6,183,082 B1 | 2/2001 | Clutterbuck | 351/160 |
| 6,199,986 B1 | 3/2001 | Williams et al. | 351/221 |
| 6,206,520 B1 | 3/2001 | Jubin et al. | 351/160 |
| 6,241,355 B1 | 6/2001 | Barsky | 351/177 |
| 6,270,218 B1 | 8/2001 | Clutterbuck | 351/160 |
| 6,305,802 B1 | 10/2001 | Roffman et al. | 351/212 |
| 6,364,483 B1 | 4/2002 | Grossinger et al. | 351/161 |
| 6,379,005 B1 | 4/2002 | Williams et al. | 351/211 |
| 6,390,624 B1 | 5/2002 | Hough | 351/177 |
| 6,406,145 B1 | 6/2002 | Jubin | 351/177 |
| 6,454,409 B1 | 9/2002 | Lorenz et al. | 351/160 |
| 6,467,903 B1 | 10/2002 | Black | 351/160 |
| 6,474,814 B1 | 11/2002 | Griffin | 351/161 |
| 6,491,392 B1 | 12/2002 | Roffman et al. | 351/160 |
| 6,568,990 B1 | 5/2003 | Siders et al. | 451/5 |
| 6,585,375 B1 * | 7/2003 | Donitzky et al. | 351/219 |
| 6,595,639 B1 | 7/2003 | Ho et al. | 351/177 |
| 6,609,793 B1 | 8/2003 | Norrby et al. | 351/212 |
| 6,626,535 B1 | 9/2003 | Altmann | 351/177 |
| 6,652,098 B1 | 11/2003 | Suzaki et al. | 351/177 |
| 6,755,524 B1 | 6/2004 | Rubinstein et al. | 351/177 |
| 2002/0105617 A1 | 8/2002 | Norrby et al. | 351/177 |
| 2003/0016331 A1 | 1/2003 | Mandell | 351/161 |
| 2003/0053025 A1 * | 3/2003 | Turner et al. | 351/205 |
| 2003/0081171 A1 | 5/2003 | Griffin | 351/161 |

FOREIGN PATENT DOCUMENTS

| | | |
|---|---|---|
| EP | 1 011 006 | 6/2000 |
| WO | WO 84/04401 | 11/1984 |
| WO | WO 92/01417 | 2/1992 |
| WO | WO 94/23327 | 10/1994 |
| WO | WO 00/10448 | 3/2000 |
| WO | WO 00/48036 | 8/2000 |
| WO | WO 01/11418 | 2/2001 |

* cited by examiner

AUTOMATIC LENS DESIGN AND MANUFACTURING SYSTEM

This application is a national stage filing under 35 U.S.C. 371 of International Application No. PCT/EP02/04649 filed Apr. 26, 2002, which claims benefits of U.S. Provisional Patent Application Nos. 60/287,189 filed Apr. 27, 2001 and 60/313,898 filed Aug. 21, 2001.

FIELD OF THE INVENTION

The present invention relates to a system and method for designing and/or producing a customized ophthalmic lens, in particular an ophthalmic lens capable of correcting high order monochromatic aberrations of eyes. In addition, the present invention discloses a method and system for creating an individualized computational model eye useful for evaluating/optimizing the optical design of an ophthalmic lens capable of correcting high order monochromatic aberrations, a method and system for creating and producing stock keep units of ophthalmic lenses capable of correcting high order monochromatic aberrations of an eye, a system and method for manufacturing an ophthalmic lens which is capable of correcting high order monochromatic aberrations, a system and method for characterizing the metrology of ophthalmic lenses, and a method for placing an order of a customized ophthalmic lens.

BACKGROUND

There has been and continues to be a need to provide an individual with improved visual acuity or visual benefit. One of known solutions is to use contact lenses in correcting adverse vision conditions. Current contact lenses have a relatively simple surface design and generally are rotationally-symmetric or toric. These contact lenses are able to correct low-order aberrations of the human eye, such as defocus, astigmatism and prism. For people who only have these low-order monochrmoatic aberrations of the eyes, their visual acuity can be improved to 20/20 or better by wearing current contact lenses. However, current contact lenses are unable to correct high-order monochromatic aberrations of the human eye, such as a non-standard amount of spherical aberration, coma, and other irregular high-order aberrations. These high order aberrations blur images formed on the retina, which can impair vision. The impact of these higher-order aberrations on retinal image quality can become significant in some cases, for example, in older eyes, in normal eyes with large pupils, and in the eyes of many people with irregular astigmatism, keratoconus, corneal dystrophies, post penetrating keratoplasty, scarring from ulcerative keratitis, corneal trauma with and without surgical repair, and sub-optimal outcome following refractive surgery. For those people, visual acuity of 20/20 or better can be achieved with customized contact lenses or contact lenses capable of correcting high-order monochromatic aberrations of the human eye.

Unlike current contact lenses, customized contact lenses or contact lenses capable of correcting high order aberrations inevitably need to have a complex surface design and/or a spatial distribution of index of refraction. The design, production and metrology-characterization of such contact lenses with complex surfaces and spatial distribution of index of refraction can not be met by current lens designing, manufacturing and characterizing technologies.

U.S. Pat. No. 6,241,355 discloses a method of computer-aided contact lens design using spline-based mathematical surfaces without restrictions of rotational symmetry. The patent teaches that each of the anterior surface, posterior surface and peripheral edge system of a contact lens can be described by one or a plurality of piecewise functions that satisfy a set of associated constraints of smoothness and thereby a contact lens can be produced to have a posterior surface that provides a good fit to a cornea having a complicated shape. However, the patent does not disclose how to design and fabricate a contact lens capable of correcting high-order aberrations, nor suggest that the design and fabrication of a contact lens capable of correcting high-order aberrations can be accomplished.

U.S. Pat. Nos. 5,777,719 and 6,095,651 disclose a concept that contact lenses for correcting at least third-order wavefront aberrations of the living eye might be fabricated based on a final correction signal that control a deformable mirror to compensate for the aberrations of the living eye. Although the patents teach that high-order aberrations of the human eye can be measured by using a Hartmann-Shack wavefront sensor and then corrected in a closed feedback loop with a deformable mirror as a compensating optical component, there are no methods or algorithms defined for converting the final correction signal, that controls a reflective optics (i.e., a deformable mirror) to compensate for the aberrations, into a signal, that produces a refractive optics (i.e., a contact lens) capable of correcting the aberrations, nor examples which shows that a contact lens can be fabricated to correct high-order aberrations.

U.S. Pat. No. 6,086,204 discloses a method for correcting the optical aberrations beyond defocus and astigmatism of an eye fitted with an original contact lens having a known anterior surface shape by providing a modified or new contact lens which has its anterior surface reshaped from said original contact lens's anterior surface. The patent teaches that a modified or new contact lens is produced by first measuring the optical aberrations of an eye fitted with an original contact lens, then performing a mathematical analysis of the eye's optical aberrations when fitted with the original contact lens to determine the modified anterior surface shape, and finally fabricating the modified anterior surface by methods that remove, add or compress material or alter the surface chemistry. There are some limitations in the method disclosed in U.S. Pat. No. 6,086,204. First, the posterior surface is not variable and is predetermined by the original contact lens. Second, a first contact lens, that is unable to correct high-order aberrations, must be fabricated, then be tried on by a patient, and finally be modified or a new contact lens having a posterior surface identical to that of the original contact lens is fabricated. The method disclosed in U.S. Pat. No. 6,086,204 could have a long lens design cycle and concept evaluation time.

WO-A-01/11418 discloses a system and method of integrating corneal topographic data and ocular wavefront data with primary ametropia measurements to create a soft contact lens design. WO-A-01/11418 teaches that a better fitting soft contact lens can be designed by achieving a contact lens back surface which is uniquely matched to a particular corneal topography, or which is an averaged shape based on the particular corneal topography. However, WO-A-01/11418 does not disclose nor suggest how to design and fabricate a contact lens capable of correcting high-order aberrations.

There still remains a need for a system and method for designing and/or fabricating contact lenses capable of correcting high-order aberrations of an eye. There is also a need for a system and method for characterizing the metrology of a contact lens capable of correcting high-order aberrations of an eye.

SUMMARY OF THE INVENTION

It is a primary objective of the present invention to provide a system and method for designing a customized ophthalmic lens.

It is also an objective of the present invention to provide a system and method for producing a customized ophthalmic lens.

It is a further objective of the present invention to provide a system and method for manufacturing customized ophthalmic lenses.

It is still a further objective of the present invention to provide a system and method for characterizing the metrology of a customized ophthalmic lens or an ophthalmic lens capable of correcting high order aberrations.

These and other objectives are achieved by the various aspects of the invention described herein.

The invention, in one aspect, provides a method for creating a computational model eye which reproduces aberrations of an eye of an individual and can find particular use in the design and production of a customized ophthalmic lens or an ophthalmic lens capable of correcting high-order aberrations. The computational model eye comprises: at least one refractive optical element having a first surface with a topography identical to the corneal topography and a second surface and a model retina having a model fovea having a lattice of pixels. The aberrations of an eye are reproduced by the optical element alone or in combination with at least one additional optical element. The method for creating a computational model eye comprises the steps of: (1) providing a set of characteristic data of an eye of an individual, wherein said set of characteristic data comprise wavefront aberrations of the eye and corneal topography data; (2) converting the corneal topography data into a mathematical description representing a first surface of a first refractive optical element, the first optical refractive element having the first surface and an opposite second surface; (3) designing and optimizing the second surface of the first refractive optical element so that the first refractive optical element, alone or in combination with a second refractive optical element that has a third surface and an opposite fourth surface and an index of refraction distribution, reproduces the wavefront aberrations of the eye; (4) designing a model retina that has a curvature of the human retina and comprises a model fovea having a lattice of pixels representing photoreceptors; and (5) arranging the first refractive optical element and the model retina along an optical axis in a way such that the distance between the fovea and the center of the first surface of the first refractive optical element is equal to the visual axial length of the human eye. Preferably, the computational model eye comprises a model crystalline lens as the second refractive optical element and a model cornea as the first refractive optical element, wherein the model crystalline lens is constructed on the basis of the crystalline lens of the human eye. In this preferred embodiment, the model cornea, the model crystalline lens and the model retina are arranged in a way identical to their corresponding elements in the human eye. More preferably, the computational model eye further comprises a pupil with a pupil size ranging from 2.0–8.0 mm, adjustable according to the individual's age and/or illumination light intensity.

The invention, in another aspect, provides an iterative process for optimizing an optical design of an ophthalmic lens. The iterative process comprising the steps of: (1) determining visual performance information of the optical design of an ophthalmic lens with a computational model eye that reproduces aberrations of an eye of an individual, wherein the computational model eye comprises a lens-supporting surface having corneal topography of the eye and a model retinal having a curvature of the human retina and a model fovea comprising a lattice of pixels that represent photoreceptors, wherein the distance between the model fovea and the center of the lens-supporting surface is equal to visual axial length of the human eye; (2) modifying the optical design of the ophthalmic lens on the basis of the visual performance information determined in step (1); and (3) repeating steps (1) and (2) until visual performance of a modified optical design of the ophthalmic lens is optimized.

The invention, in another aspect, provides a method and system for designing a customized ophthalmic lens or an ophthalmic lens which is capable of correcting high order aberrations. The lens-designing method comprises the steps of: (1) providing a set of characteristic data of an eye of an individual, wherein said set of characteristic data comprises wavefront aberrations of the eye and corneal topography; (2) creating a computational model eye that reproduces the wavefront aberrations of the eye, wherein the computational model eye comprise a lens-supporting surface having the corneal topography of the eye and a model retinal having a model fovea comprising a lattice of pixels that represent photoreceptors, wherein the distance between the model fovea and the center of the lens-supporting surface is equal to visual axial length of the human eye; (3) designing an optical model lens which is capable of compensating for the wavefront aberrations of the eye; (4) evaluating the visual performance of said optical model lens with the computational model eye; (5) obtaining visual performance information of said optical model lens; (6) modifying the design of said optical model lens on the basis of said visual performance information to improve corrections of the aberrations of the eye if the visual performance of said optical model lens is not optimal; (7) repeating steps (4) to (6) until the visual performance of said optical model lens is optimal; and (8) transforming the optimized optical model lens into a set of mechanical parameters for making said customized ophthalmic lens or said ophthalmic lens capable of correcting high order aberrations. The lens-designing system includes a computer system comprising: (a) a model eye design module for creating a computational model eye that reproduces aberrations of an eye of an individual, wherein the computational model eye comprises a lens-supporting surface having corneal topography of the eye and a model retina having a curvature of the human retina and a model fovea comprising a lattice of pixels that represent photoreceptors, wherein the distance between the model fovea and the center of the lens-supporting surface is equal to visual axial length of the human eye; (b) an optical design module for designing an optical model lens to compensate for the wavefront aberrations of the eye and to accommodate the corneal topography of the eye of the individual or an averaged corneal topography derived from population studies, (c) a lens-designing optimization module for performing an iterative optimization process comprising (1) determining visual performance information of the optical model lens with the computational model eye, (2) modifying the design of the optical model lens on the basis of said visual performance information to improve corrections of the aberrations of the eye if the visual performance of said optical model lens is not optimal, and repeating steps (1) and (2), if necessary, until visual performance of a modified design of the optical model lens is optimized; and (d) a mechanical design module for generating a CAD output file containing parameters for making said customized ophthalmic lens or said ophthalmic lens capable of correcting high order aberrations, based on the optimized optical model lens. Preferably, the system further comprises a sensor system, which is capable of determining the set of characteristics data of the eye.

The invention, in still another aspect, provides a method and system for producing a customized ophthalmic lens or an ophthalmic lens which is capable of correcting high order aberrations. The lens-producing method comprises the eight steps of the above lens-designing method and further comprises the following steps: (9) converting the set of mechanical parameters for making the lens into control signals that control a computer-controllable manufacturing device and (10) producing the lens using the computer controllable manufacturing device. The lens-producing system includes a computer-controllable manufacturing device and a computer system comprising: (a) a model eye design module for creating a computational model eye a model eye design module for creating a computational model eye that reproduces aberrations of an eye of an individual, wherein the computational model eye comprises a lens-supporting surface having a corneal topography of the eye and a model retina having a curvature of the human retina and a model fovea comprising a lattice of pixels that represent photoreceptors, wherein the distance between the model fovea and the center of the lens-supporting surface is equal to a visual axial length of the human eye; (b) an optical design module for designing an optical model lens to compensate for the wavefront aberrations of the eye of the individual and to accommodate the corneal topography of the eye of the individual, (c) a lens-designing optimization module for performing an iterative optimization process comprising (1) determining visual performance information of the optical model lens with the computational model eye, (2) modifying the design of the optical model lens on the basis of said visual performance information to improve corrections of the aberrations of the eye if the visual performance of said optical model lens is not optimal, and repeating steps (1) and (2), if necessary, until visual performance of a modified design of the optical model lens is optimized; (d) a mechanical design module for generating a CAD output file containing parameters for making the ophthalmic lens, based on the optimized optical model lens; (e) a signal module for converting said CAD output file into control signals that control the computer-controllable manufacturing device to produce said ophthalmic lens; and (f) a manufacturing control module for controlling the computer-controllable manufacturing device to produce said ophthalmic lens. Preferably, the system further comprises a sensor system, which is capable of determining the set of characteristics data of the eye.

The invention, in a further aspect, provides a system and method for characterizing the optical metrology of an ophthalmic lens capable of correcting higher order aberrations of an eye. The metrology characterizing system comprises: (a) a monochromatic point light source; (b) a diffraction limited model eye in front of said monochromatic point light source, wherein said model eye has a posterior surface and an opposite anterior surface having an averaged corneal topography of a population; (c) a lubricating system to simulate a tear film on the anterior surface of the model eye; (d) an aperture which simulates the human fovea and is located between said light source and said model eye, wherein said simulated fovea is capable of moving along the light path via manual means or via a precision motion control system to null defocus; and (e) a wavefront sensor in front of said model eye. Preferably, the metrology system further comprises an additional aperture to simulate the pupil or iris of the eye, wherein the additional aperture is located along the optical pathway between the wavefront sensor and the refractive optics. The optical metrology characterizing method comprises (1) installing said contact lens in the above metrology system and (2) characterizing the metrology of said contact lens.

The invention, in another further aspect, provides a method for manufacturing ophthalmic lenses capable of correcting aberrations of eyes. The lens-manufacturing method of the invention comprises the steps of: (1) analyzing eyes of each of the individuals from a population to obtain a set of characteristic data comprising aberrations and corneal topography; (2) compiling population statistics of aberrations and corneal topographies; (3) creating a plurality of computational model eyes, each of which generates averaged aberrations representing statistically one of a plurality of nominal segments of the population, wherein each of plurality of computational model eyes comprises a lens-supporting surface having an averaged corneal topography for one of a plurality of nominal segments of the population and a model retina having a model fovea comprising a lattice of pixels that represent photoreceptors, wherein the distance between the model fovea and the center of the lens-supporting surface is equal to a visual axial length of the human eye; (4) designing a plurality of optical model lenses each of which accommodates the averaged corneal topography of the eyes of one of the plurality of nominal segments of the population and corrects the averaged aberrations of the eyes of one of the plurality of nominal segments of the population; (5) optimizing optical designs of the plurality of the optical model lenses with one of the plurality of the computational model eyes; (6) transforming the plurality of the optimized optical model lenses into a plurality of sets of mechanical parameters each for making one contact lens; (7) creating one stock keeping unit (SKU) for each of each of the contact lenses; and (8) manufacturing said ophthalmic lenses having a specific SKU.

The invention, in still a further aspect, provides a method for ordering a pair of customized contact lenses, the method comprising the steps of: (1) providing wavefront aberrations and corneal topographies of the first and second eyes of a patient to a client computer system; (2) sending a first request, under control of the client computer system, to look for a pair of customized contact lenses capable of correcting the aberrations of both eyes, to a server system; (3) receiving the first request by the server system; (4) converting the wavefront aberrations and corneal topographies into a querying order in a format readable by a query engine in the server system; (5) using the querying order to search against a SKU database to obtain a first and a second list of SKUs, wherein each of the SKUs in the first list is capable of accommodating adequately the corneal topography of the first eye and of correcting adequately the wavefront aberrations of the first eye, wherein each of the SKUs in the second list is capable of accommodating adequately the corneal topography of the second eye and of correcting adequately the wavefront aberrations of the second eye; (6) displaying lens information related to each of the two list of SKUs with SKU identifiers under control of the client computer system; (7) selecting a pair of SKUs with a first SKU identifier and a second SKU identifier under control of the client computer system or a choice to make a new pair of customized contact lenses; (8) sending a second request to order a pair of contact lenses with the first and the second SKU identifier or to order the new pair of customized contact lenses to be made, along with a customer identifier that identifies the patient and/or an eye-care practitioner who takes care of the patient, under control of the client computer system; (9) receiving the second request by the server system; (10) retrieving additional information previously stored for the patient and/or the eye-care practitioner identified by the customer identifier in the received second request; and (11) generating an order to deliver the pair of customized lenses for the patient or the eye-care practitioner identified by the customer identifier in the received second request using the retrieved additional information.

The invention, in still another further aspect, provides a client computer system for ordering pairs of customized contact lenses and a server system for generating order for pairs of customized contact lenses.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRPTION OF THE DRAWINGS

FIG. 1 is a schematic representation of a system for designing and producing an ophthalmic lens capable of correcting high order aberrations according to a preferred embodiment of the present invention.

FIG. 2 schematically depicts a process for designing and producing an ophthalmic lens capable of correcting high order aberrations according to a preferred embodiment of the present invention.

FIG. 3 schematically shows a reduced computational model eye according to a preferred embodiment of the invention.

FIG. 4 schematically shows an anatomical computational model eye according to a preferred embodiment of the invention.

FIG. 5 schematically shows a metrology system according to a preferred embodiment of the invention.

DESCRIPTION OF THE PREFERRED EMBODIMENTS

Figure 1:
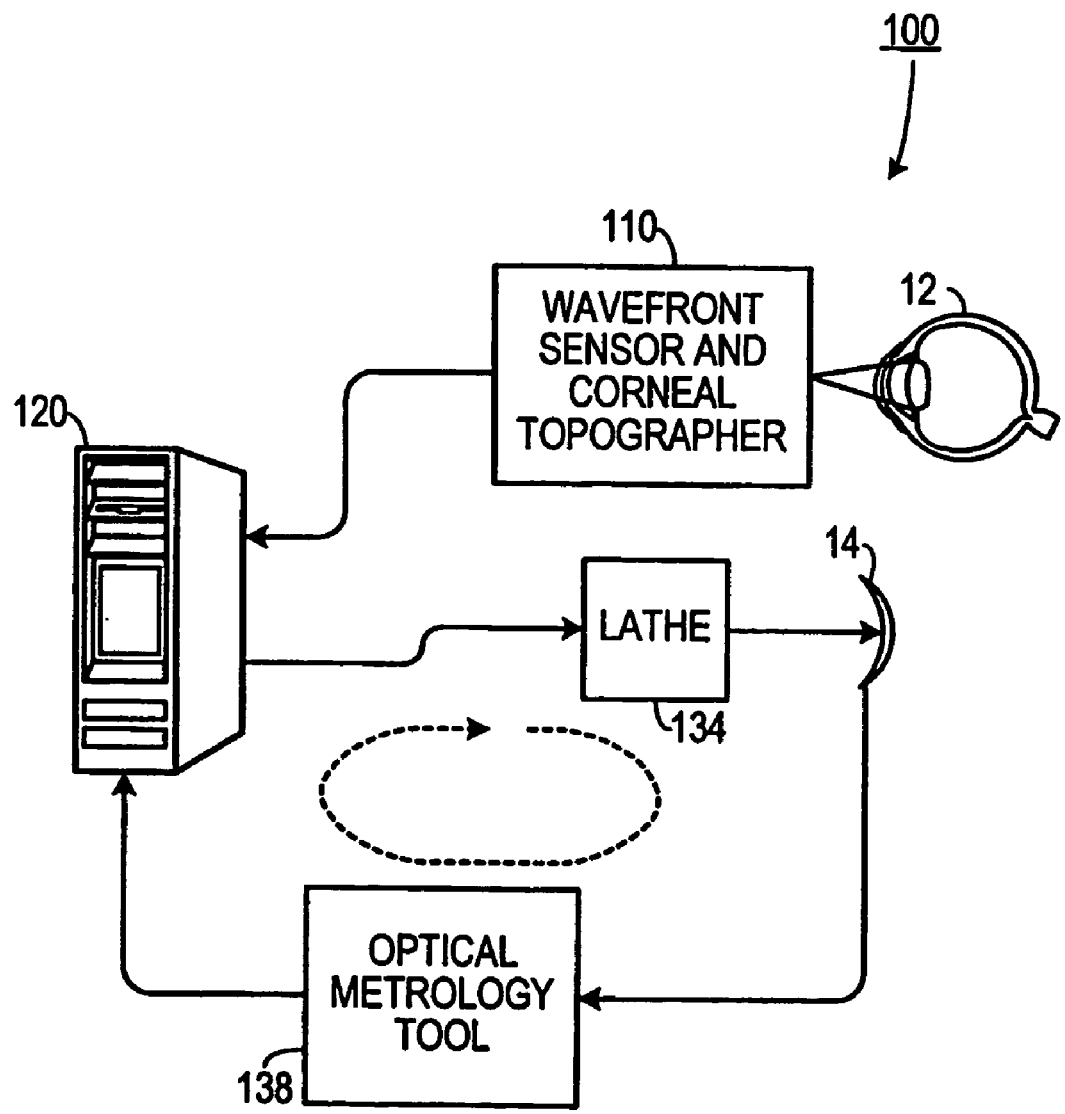

A preferred embodiment of the invention is a method for creating a reduced computational model eye, the method comprising: (1) providing a set of characteristic data of an eye of an individual, wherein said set of characteristic data comprise wavefront aberrations and corneal topography data of the eye of an individual; (2) converting the corneal topography data into a mathematical description representing the anterior surface of a model lens; (3) designing and optimizing the posterior surface of the model lens so that the model lens reproduces the wavefront aberrations of the eye of the individual; (4) designing a model retina that has a curvature of the human retina and comprises a model fovea having a lattice of pixels representing photoreceptors, and (4) arranging the model lens and the model retina along an optical axis in a way such that the distance between the model fovea and the vertex of the anterior surface of the model lens is equal to visual axial length of the human eye.

"A computational model eye" as used herein refers to an interactive computer optical model that represents the optical characteristics of an eye of an individual, preferably in a relaxed state.

"A reduced computational model eye" as used herein refers to an interactive computer optical model that comprises: (1) a model lens having a posterior surface and an anterior surface having the corneal topography of an eye of an individual, wherein the model lens is capable of duplicating aberrations of that eye; and (2) a model retina that has a curvature of the human retina and a model fovea comprising a hexagonal lattice of pixels, preferably 2.5 micron pixels, representing photoreceptors, wherein the retina is placed along an optical axis such that the distance between the model fovea and the center of the anterior surface of the model lens is identical to the visual axial length of the human eye. Preferably, a reduced computational model eye further comprises a model pupil located between the model lens and the model retina. The size of the model pupil is about from 2.0 mm to 8.0 mm and adjustable according to the individual's age and/or illumination light intensity. Preferably, the size of the model fovea is about 2 mm.

"The posterior surface of the model lens" refers to the surface of the model lens which is facing toward the retina in a reduced computational model eye. "The anterior surface of a model lens" refers to the surface on which a contact lens can be placed.

"An optical axis" refers to a line of best fit through the centers of curvatures of surfaces of all refractive optical elements and the model fovea in a computation model eye. The optical axis of the human eye refers to the line of best fit through centers of curvatures of the refracting surfaces.

"The human eye" means an eye that represents statistically all normal eyes of a given population. The human eye comprises the human cornea, the human crystalline lens, and the human retina. "The human retina" means a retina that represents statistically retinas of all normal eyes of a given population. "The human cornea" refers to a cornea that represents statistically corneas of all normal eyes of a given population.

The term "visual axial length" refers to the distance between the ophthalmometric pole and the fovea along the visual axis of the relaxed eye. The ophthalmometric pole refers to the intercept of the visual axis at the anterior surface of the cornea of the relaxed eye. The visual axis of the human eye refers to the line joining a fixation point and the foveal image by way of the nodal points.

Figure 3:
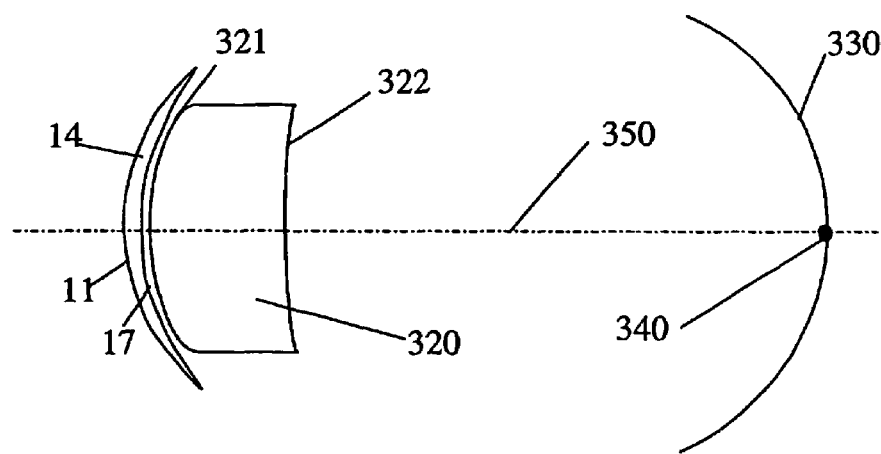

FIG. 3 schematically shows a reduced computational model eye according to a preferred embodiment of the invention. A model lens 320 has a posterior surface 322 and an opposite anterior surface 321. A contact lens 14 having a posterior (concave) surface (or base curve) 17 and an anterior (convex) surface (or front curve) 11 is placed on the anterior surface 321 of the model lens 320. The optical axis 350 of the model lens 320 passes through the center of a model fovea 340 in a model retina 330 which has a curvature of the human retina. The model fovea 340 has a size of about 2.0–8.0 mm and comprises a hexagonal lattice of 2.5 micron pixels (not shown). The distance between the model fovea 340 and vertex of the anterior surface 321 is identical to the visual axial length of the eye of an individual.

Another preferred embodiment is a method for creating an anatomical computational model eye, the method comprising: (1) providing a set of characteristic data of an eye of an individual, wherein said set of characteristic data comprise wavefront aberrations and corneal topography data of the eye of the individual; (2) creating a model crystalline lens having a refractive power range equal to that of the natural crystalline lens of the human eye; (3) converting the corneal topography data into a mathematical description representing the anterior surface of a model cornea; (4) designing and optimizing the posterior surface of the model cornea so that the combination of the model cornea and the model lens reproduces the wavefront aberrations of the eye of the individual; (5) designing a model retina that has a curvature of the human retina and comprises a model fovea having a hexagonal lattice of pixels representing photoreceptors; and (5) arranging the model cornea, the model crystalline lens and the model retina along an optical axis in a way such that the distance between the fovea and the vertex of the anterior surface of the model cornea is equal to visual axial length of the human eye. In a preferred embodiment, the size of pixels is about 2.5 micron and the size of the model fovea is 2 mm in diameter.

"An anatomical computational model eye" as used herein refers to an interactive computer optical model that is capable of duplicating aberrations of an eye of an individual and comprises at least the following three optical elements: a model cornea having the corneal topography of the eye of the individual, a model crystalline lens which preferably represents a natural crystalline lens typically for an age group of a population, and a model retina having a fovea that has a curvature of the human retina and a model fovea comprising a hexagonal lattice of pixels, preferably 2.5 micron pixels, representing photoreceptors. All the optical elements are arranged along an optical axis in a way identical to their arrangement in the human eye, wherein the distance between the fovea and the vertex of the model cornea is equal to visual axial length of the human eye. The arrangement of the optical elements in an anatomical computational model eye refers to their position relative to each other along the optical axis. For example, the position of the crystalline lens relative to the retina is defined by an optical axial distance between the posterior surface of the crystalline lens and the fovea. The value of the optical axial distance between the posterior surface of the crystalline lens and the fovea is well known and can be found in literatures and books. Preferably, an anatomical computational model eye further comprises a pupil located between the model cornea and the model crystalline lens. The size of the model pupil is about from 2.0 mm to 8.0 mm and adjustable according to the individual's age and/or illumination light intensity. More preferably, an anatomical computational model eye further comprises other refractive elements in the eye, such as fluids in the anterior and posterior chambers.

An anatomical computational model eye of the invention is an anatomically correct representation of the eye and has additional degrees of freedom which allow for a more complete description of dynamic imaging for modeling presbyopia.

"The posterior surface of the model cornea" refers to the surface that has a concave curvature and that is facing toward the model crystalline lens. "The anterior surface of a model lens" refers to the surface having a convex curvature, on which a contact lens can be placed.

Figure 4:
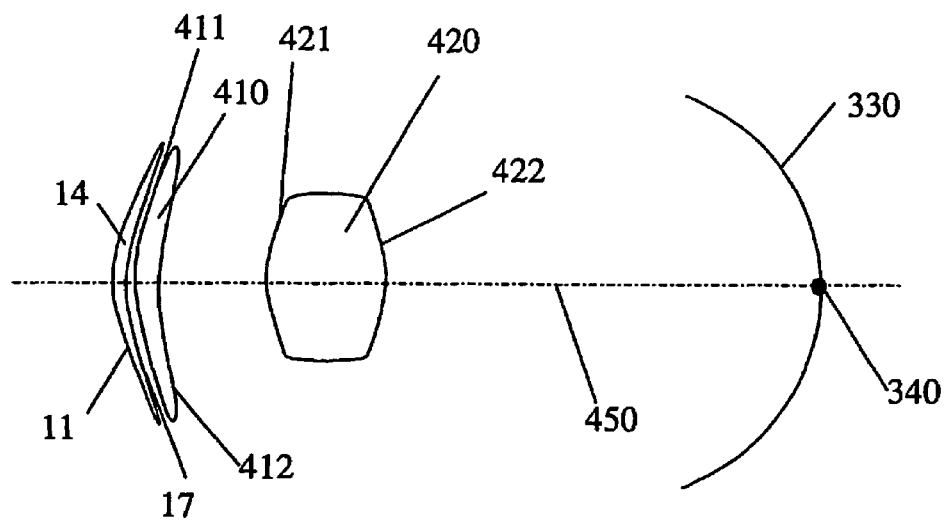

FIG. 4 schematically shows an anatomical computational model eye according to a preferred embodiment of the invention. A model cornea 410 has a posterior surface 412 and an opposite anterior surface 411. A contact lens 14 having a posterior (concave) surface (or base curve) 17 and an anterior (convex) surface (or front curve) 11 is placed on the anterior surface 411 of the model cornea 410. An optical axis 450 is the line of best fit through the centers of curvatures of all surfaces of the model cornea 410, a model crystalline lens 420 and a model fovea 340 in a model retina 330. The model retina 330 has a curvature of the human retina. The model crystalline lens 420 has a first convex surface 421, an opposite second convex surface 422 and a midplane. The model fovea 340 has a size of 2 mm in diameter and comprises a hexagonal lattice of 2.5 micron pixels (not shown). The distance between the model fovea 340 and vertex of the anterior surface 411 of the model cornea 410 is identical to the visual axial length of the eye of an individual. The optical axial distance from the model fovea to the posterior surface of the model crystalline lens is 7.68 mm.

The wavefront aberrations of an eye of an individual can be determined by any suitable methods known to one skilled in the art. For example, Liang et al. in J. Optical Soc. Am. 11:1–9, the entirety of which are herein incorporated by reference, teach how to determine wavefront aberrations of an eye at various pupil diameters using a Hartmann-Shack system. The wavefront aberrations generally are quantified in Zernike polynomials which are a set of functions that are orthogonal over the unit circle. Since Zernike polynomials are orthogonal, the aberrations are separable and can be treated as such. The first order Zernike modes are the linear terms. The second order Zernike modes are the quadratic terms, which correspond to the aberrations such as defocus and astigmatism. The third order Zernike modes are the cubic terms, which correspond to the coma and coma-like aberrations. The fourth order Zernike modes contain spherical aberrations as well as other modes. The fifth Zernike modes are the higher-order, irregular aberrations. Local irregularities in the wavefront within the pupil are represented by these higher-order Zernike modes. "High-order" aberrations of an eye as used herein refers to monochromatic aberrations beyond defocus and astigmatism, namely, third order, fourth order, fifth order, and higher order wavefront aberrations.

Corneal topographic data can be acquired using a corneal topographer or videokeratoscope. Corneal topography data may be in any forms suitable for use in designing an ophthalmic lens. Exemplary forms include, but are not limited to, Zernike polynomials, point cloud data and the like. Preferably, corneal topography data are in a form in which the wavefront aberrations of an eye are quantified. The corneal topography data contained in the set of characteristic data of an eye can also be an averaged corneal topography derived from population studies. Such averaged corneal topography data may optionally be incorporated as a parameter in algorithms for creating a computational model eye.

Visual axial length of the human eye refers to a visual axial length that represents statistically the visual axial length of eyes of a given population. The value of the visual axial length of the human eye can be found in the literatures and books and may be incorporated as a parameter in the algorithms for creating a computational model eye. Preferably, the visual axial length is the actually measured visual axial length of an eye of an individual.

The set of characteristic data of an eye of an individual can also be a set of known characteristic data that represent statistically a nominal segment of population on the basis of population studies. Such set of characteristic data of the eye can be used in the designing and manufacturing of customized ophthalmic lenses. Furthermore, a plurality of such set of characteristic data of the eye can be used in creating and producing stock keeping units (SKUs) of customized ophthalmic lenses.

"A customized ophthalmic lens", as used herein, means: (1) an ophthalmic lens that has one of the surfaces accommodating the corneal topography of an eye of an individual and/or can correct high order aberrations of the eye or that has an asymmetrical surface design and/or can correct high order aberrations of the eye; (2) an ophthalmic lens that is designed using input of aberration measurements of an eye of an individual; or (3) an ophthalmic lens with bifocal, multi-focal or progressive multifocal properties, that is designed using input of aberration measurements of an eye of an individual.

In a more preferred embodiment, the set of characteristic data further comprises corneal pachymetry data. Such additional data are useful for building an anatomical computational model eye. The posterior surface of the model cornea can be generated on the basis of the anterior surface topography and the corneal pachymetry data. Such anatomical computational model eye can find particular use in designing and producing customized intraocular lenses, as described below.

U.S. Pat. No. 5,963,300, herein incorporated by reference in its entirety, discloses a single system and methods for measuring wavefront aberrations, corneal topographic data, corneal pachymetry, pupil size, retinal acuity, ocular acuity, etc.

There are many kinds of mathematical functions that can be used to describe the corneal topography of an eye. Exemplary mathematical functions include conic and quadric, polynomials of any degree, Zernike polynomials, exponential functions, trigonometric functions, hyperbolic functions, rational functions, Fourier series, and wavelets. Preferably, a combination of two or more mathematical functions are used to describe the corneal topography of an eye. More preferably, Zernike polynomials are used to describe the corneal topography of an eye. Even more preferably, Zernike polynomials and spline-based mathematical functions are used together to describe the corneal topography of an eye. An individual skilled in the art will know how to convert the corneal topography data of an eye into a mathematical description (one or more mathematical functions) representing the corneal topography of an eye. Such mathematical description can be used as the anterior surface of a model lens in a reduced computational eye model or as the anterior surface of a model cornea in an anatomical computational eye model.

The posterior surface of a model lens in a reduced computational model eye in a form of mathematical description can be designed, for example, by subtracting the optical aberrations derived from the corneal topography from the wavefront aberrations of an eye, or by ray tracing of the anterior surface of the model lens. The ray tracing technique is well known in the art. Several commercially-available optical design software packages contain ray tracing programs. Exemplary optical design software packages include Zemax from Focus Software, Inc. and Advanced System Analysis program (ASAP) from Breault Research Organization.

Preferably, a mathematical description for the posterior surface of the model lens in a reduced computational model eye is polynomials, the coefficients of which can be optimized in an optimization routine such as a least square fit or equivalent to generate the optimized posterior surface which allow the model lens to reproduce the wavefront aberrations of the eye. More preferably, a set of aberration coefficients, that represent the wavefront aberrations of an eye, are used as weighted operands in an optical design optimization loop to optimize the posterior surface of the model lens so that the reduced computational model eye can reproduce the wavefront aberrations of the eye.

The posterior surface of a model cornea in an anatomical computational model eye can be designed, for example, by subtracting the optical aberrations derived from both the corneal topography (the anterior surface of the model cornea) and a model crystalline lens from the aberrations of the eye, or by ray tracing of the anterior surface of the model cornea. Preferably, a mathematical description is polynomials, the coefficients of which can be optimized in an optimization routine such as a least square fit or equivalent to generate the optimized posterior surface which allow the anatomical computation model eye to reproduce the wavefront aberrations of the eye. More preferably, a set of aberration coefficients, that represent the wavefront aberrations of an eye, are used as weighted operands in an optical design optimization loop to optimize the posterior surface of the model cornea so that the anatomical computational model eye can reproduce the wavefront aberrations of the eye.

The refractive power range of the model crystalline lens in an anatomical computational model eye generally can be generated based on any combinations of the surface topographies and the index of refraction distribution. For example, the topographies and the index of refraction distribution of a natural crystalline lens in the eye representing an age group of a population can be used directly to generate the model crystalline lens in an anatomical computational model eye. Data, such as the topographies of the two surfaces, index of refraction distribution and the refractive power range of the crystalline lens of the human eye, can be found from literatures and reference books, for example, Optics of the Human Eye, (Atchison and Smith, eds.), Butterworth-Heinemann: Boston 2000 and Liou et al., J. Opt. Soc. Am. 14: 1684–1695. Alternatively, based on a single index of refraction, the topographies of the two surfaces of the model crystalline lens can be varied and optimized to obtain a desired refractive power range corresponding to that of the natural crystalline lens in the human eye.

In a preferred embodiment, presbyopia information is also preferably incorporated in creating the refractive power range of the model crystalline lens in an anatomical computational model eye. It is believed that as an individual ages the natural crystalline lenses of the eyes tend to harden, thicken and the surfaces become steeper. The hardening makes it difficult for the eye crystalline lens to change its surface curvature (i.e. bending). This inability of the eye crystalline lens to bend is a condition referred to as presbyopia.

In a preferred embodiment, the age of an individual is taken into account for creating a model pupil in a computational model eye, particularly for adjusting the pupil size. The manner in which the size of an individual's pupil varies is predictable, principally depending on the illumination level and the age of the individual. For people of the same age, the size of their pupils at maximum and minimum dilation changes as a function of illumination level, in the same or substantially the same way. Thus, the size of an individual's pupils at minimum and maximum dilation can be estimated based upon the age of that individual. A pupil with appropriate size will be particularly useful for evaluating the design of a lens for correcting presbyopia.

In the algorithm used for building a computational model eye, the chromatic dispersion and Stiles-Crawford effects are preferably incorporated.

The computational model eye of the present invention can find use in evaluating the visual performance of the optical design of an ophthalmic lens by determining merit functions such as point spread function (PSF), line spread function (LSF), modulation transfer function (MTF), phase transfer function, contrast threshold function, contrast sensitivity function (CSF) and other merit functions known or constructed by those skilled in the art. A computational model eye of the invention can also used in performing bitmap image analysis, ghost image analysis, and focal length and optical power analysis, because the computational model eye contains a model retina having a model fovea having a hexagonal lattice of pixels that represent photoreceptors. The bitmap image analysis and ghost image analysis are very useful information for optimizing bifocal/multifocal lens design. Visual performance information of an optical design of an ophthalmic lens is useful for optimizing the optical design of that lens.

For evaluating the visual performance of the optical design of a contact lens, the contact lens is placed on the anterior surface of the first refractive optical element in a computational model eye.

When evaluating the visual performance of the optical design of an aphakic intraocular lens, the model crystalline lens is first deleted from an anatomical computational model eye and then the aphakic intraocular lens is placed in a position between the model cornea and the model crystalline lens. When evaluating the visual performance of the optical design of a phakic intraocular lens, the phakic intraocular lens is placed between the model cornea and the model crystalline lens. Preferably, the anatomical computational model eye comprises a model cornea which is created based on the corneal topography and pachymetry data of an eye.

The computational model eye of the present invention may find use in estimating the visual acuity of the optical design of an ophthalmic lens by determining merit functions such as point spread function (PSF), line spread function (LSF), modulation transfer function (MTF), phase transfer function, contrast threshold function, contrast sensitivity function (CSF) and other merit functions known or constructed by those skilled in the art, and by performing bitmap image analysis, ghost image analysis, and focal length and optical power analysis.

Another preferred embodiment of the invention is an iterative process for optimizing an optical design of an ophthalmic lens, the iterative process comprising the steps of: (1) determining visual performance information of the optical design of an ophthalmic lens with a computational model eye that reproduces aberrations of an eye of an individual, wherein the computational model eye comprises a lens-supporting surface having the corneal topography of the eye and a model retina having a model fovea comprising a hexagonal lattice of pixels that represent photoreceptors, wherein the distance between the model fovea and the center of the lens-supporting surface is equal to a visual axial length of the human eye; (2) modifying the optical design of the ophthalmic lens on the basis of the visual performance information determined in step (1); and (3) repeating steps (1) and (2) until visual performance of a modified optical design of the ophthalmic lens is optimized. Preferably, the visual performance information comprises at least a merit function selected from the group consisting of point spread function (PSF), modulation transfer function (MTF), bitmap image analysis, ghost image analysis, focal length analysis and optical power analysis.

Another preferred embodiment of the invention is a method for designing a customized ophthalmic lens, comprising the steps of: (1) providing a set of characteristic data of an eye of an individual, wherein said set of characteristic data comprise wavefront aberrations and corneal topography of the eye of the individual; (2) creating a computational model eye capable of duplicating the wavefront aberrations of the eye of the individual, wherein the computational model eye comprises a lens-supporting surface having the corneal topography of the eye of the individual and a model retina having a model fovea comprising a lattice of pixels that represent photoreceptors, wherein the distance between the model fovea and the vertex of the lens-supporting surface is equal to the visual axial length; (3) designing an optical model lens which is capable of compensating for the wavefront aberrations of the eye of the individual; (4) evaluating the visual performance of said optical model lens with the computational model eye; (5) obtaining visual performance information of said optical model lens; (6) modifying the design of said optical model lens on the basis of said visual performance information to improve corrections of the aberrations of the eye, if the visual performance of said optical model lens is not optimal; (7) repeating steps (3) to (6), if necessary, until the visual performance of said optical model lens is optimal; and (8) transforming the optical model lens having optimal visual performance into a set of mechanical parameters for making said customized ophthalmic lens.

"A lens-supporting surface" as used herein refers to the anterior surface of a model lens in a reduced computational model eye or the anterior surface of a model cornea in an anatomical computational model eye.

"An optical model lens" refers to an ophthalmic lens that is designed in a computer system and generally does not contain other non-optical systems which are parts of an ophthalmic lens. Exemplary non-optical systems of a contact lens include, but are not limited to bevel, lenticular, and edge that joins the anterior and posterior surfaces of a contact lens.

"A bevel" refers to a non-optical surface zone located at the edge of the posterior surface of a contact lens. Generally, the bevel is a significantly flatter curve and is usually blended with the base curve (optical posterior surface) of a contact lens and appears as an upward taper near the edge. This keeps the steeper base curve radius from gripping the eye and allows the edge to lift slightly. This edge lift is important for the proper flow of tears across the cornea and makes the lens fit more comfortable.

"A lenticular" refers to a non-optical surface zone of the anterior surface of a contact lens between the optical zone and the edge. The primary function of the lenticular is to control the thickness of the lens edge.

It is well known to those skilled in the art that the optical power of a contact lens is, inter alia, a function of the index of refraction of the lens material and the algebraic difference between the curvatures of the anterior surface and the posterior surface of the lens. Generally when designing a customized contact lens or a contact lens capable of correcting high-order aberrations of an eye, the posterior surface of the lens is first designed to accommodate the corneal topography of that eye or a corneal topography statistically representing a segment of a population. A posterior surface with such design will provide a good or adequate fit to the cornea of an eye and therefore enhance the wearer's comfort. The anterior surface of the lens then is designed and optimized so that the designed lens compensates for the aberrations of that eye.

It is believed that the posterior surface of a contact lens does not need to match perfectly the corneal topography of an eye. A perfect match means the posterior surface of a contact lens is exactly superimposable on a corneal topography. A contact lens, which has a posterior surface perfectly matching the corneal topography of an eye, may have inadequate on-eye movement of the lens and may have an adverse impact on wearer's comfort.

When designing a contact lens capable of correcting presbyopia of an individual, it is preferable to incorporate the following optical design parameters including, but not limited to, pupil diameter range, alternating/simultaneous function, monocular/binocular function, segment design (such as shape and number of zones, discrete/progressive zones, lens added power, etc.), and ages and occupational factors of that individual.

When designing a contact lens for a keratoconus patient, the base curve (concave surface) of that contact lens is preferably designed to accommodate the corneal topography of that patient.

When designing a contact lens for correcting astigmatism, one needs to take into account lens orientation and method of orientation to be used.

It is well known in the art that when a soft contact lens is placed on the eye, it conforms to the underlying shape of cornea. The extent of soft lens flexure (wrap) depends on the modulus of elasticity of lens materials. Preferably, soft lens flexure needs to be taken into account in the designing of an optical lens and in the evaluating of its visual performance with a computational model eye.

Any mathematical function can be used to describe the anterior surface, posterior surface, peripheral edge of an ophthalmic lens, as long as they have sufficient dynamic range which allow the design of that lens to be optimized. Exemplary mathematical functions include conic and quadric functions, polynomials of any degree, Zernike polynomials, exponential functions, trigonometric functions, hyperbolic functions, rational functions, Fourier series, and wavelets. Preferably, a combination of two or more mathematical functions are used to describe the front (anterior) surface and base (posterior) surface of an ophthalmic lens. More preferably, Zernike polynomials are used to describe the front (anterior) surface and base (posterior) surface of an ophthalmic lens. Even more preferably, Zernike polynomials and spline-based mathematical functions are used together to describe the front (anterior) surface and base (posterior) surface of an ophthalmic lens.

Surface topographies, index of refraction distribution, diffractive or holographic structures of a designed optical and/or mechanical model lens can be optimized according to feedback from the evaluation of its visual performance with a computational model eye. Any known, suitable optimization algorithms, for example, a least square fit or equivalent, can be used in the design optimization. Preferably, a set of aberration coefficients, that represent the wavefront aberrations of an eye, are used as weighted operands in an optical design optimization loop in the optimization of the optical design of the ophthalmic lens. More preferably, artificial intelligence (AI) programs or neural networks are used in the optimization of the optical design of the ophthalmic lens.

Any known, suitable optical computer aided design (CAD) system may be used to design an optical model lens. Exemplary optical computer aided design systems includes, but are not limited to Advanced System Analysis program (ASAP) from Breault Research Organization and ZEMAX (Focus Software, Inc.). Preferably, the optical design will be performed using Advanced System Analysis program (ASAP) from Breault Research Organization with input from ZEMAX (Focus Software, Inc.). ASAP will also preferably be used in analysis of visual performance of optical model lens.

The design of the optimized optical model lens can be transformed by, for example, a mechanical computer aided design (CAD) system, into a set of mechanical parameters for making a physical lens. Any known, suitable mechanical CAD system can be used in the invention. Preferably, the design of an optical model lens may be translated back and forth between the optical CAD and mechanical CAD systems using a translation format which allows a receiving system, either optical CAD or mechanical CAD, to construct NURBs or Beizier surfaces of an intended design. Exemplary translation formats include, but are not limited to, VDA (Verband der Automobilindustrie) and IGES (Initial Graphics Exchange Specification). By using such translation formats, overall surface of lenses can be in a continuous form that facilitates the production of lenses having radially asymmetrical shapes. Beizier and NURBs surfaces are particular advantageous for presbyopic design because multiple zones can be blended, analyzed and optimized. More preferably, the mechanical CAD system is capable of representing precisely and mathematically high order surfaces. An example of such mechanical CAD system is Pro/Engineer.

When transforming the design of an optimized optical model lens into a set of mechanical parameters, parameters for some common features of a family of ophthalmic lenses can be incorporated in the lens designing process. Examples of such parameters include shrinkage, non-optical edge zone and its curvature, center thickness, range of optical power, and the like.

Another preferred embodiment of the invention is a system for designing a customized ophthalmic lens, the system comprising a computer system including: (a) a model eye design module for creating a computational model eye that reproduces aberrations of an eye of an individual, wherein the computational model eye comprises a lens-supporting surface having the corneal topography of the eye and a model retina having a curvature of the human retina and a model fovea comprising a hexagonal lattice of pixels that represent photoreceptors, wherein the distance between the model fovea and the center of the lens-supporting surface is equal to the visual axial length of the human eye; (b) an optical design module for designing an optical model lens to compensate for the wavefront aberrations of the eye of the individual and to accommodate the corneal topography; (c) a lens-designing optimization module for performing an iterative optimization process comprising (1) determining visual performance information of the optical model lens with the computational model eye, (2) modifying the design of the optical model lens on the basis of said visual performance information to improve corrections of the aberrations of the eye of the individual, and repeating steps (1) and (2) until visual performance of a modified design of the optical model lens is optimized; and (d) a mechanical design module for generating a CAD output file containing parameters for making said customized ophthalmic lens or said ophthalmic lens capable of correcting high order aberrations, based on an optimized optical model lens.

Preferably, the lens designing system further comprises a sensor system, which determines a set of characteristic data of an eye of an individual. A sensor system preferably comprises a wavefront sensor. More preferably, the computer system further comprises a signal module for converting said CAD output file into control signals that control the computer-controllable manufacturing device to produce said ophthalmic lens.

Another preferred embodiment of the invention is a method for producing a customized ophthalmic lens, the method comprising: (1) designing the ophthalmic lens according to the above designing method of the present invention; (2) generating control signals that control a computer controllable manufacturing device; and (3) producing said ophthalmic lens.

A computer controllable manufacturing device is a device that can be controlled by a computer system and that is capable of producing directly an ophthalmic lens or an optical tool for producing an ophthalmic lens. Any known, suitable computer controllable manufacturing device can be used in the invention. Exemplary computer controllable manufacturing devices includes, but are not limited to, lathes, grinding and milling machines, molding equipments, and lasers. Preferably, a computer controllable manufacturing device is a two-axis lathe with a 45o piezo cutter or a lathe apparatus disclosed by Durazo and Morgan in U.S. Pat. No. 6,122,999, herein incorporated by reference in its entirety.

In a preferred embodiment, the step (2) is performed by a system that can convert a CAD output file into computer controlling signals.

Another preferred embodiment of the invention is a system for fabricating a customized ophthalmic lens or an ophthalmic lens capable of correcting high order aberrations, comprising:

(1) a computer-controllable manufacturing device and (2) a computer system comprising:

a model eye design module for creating a computational model eye that reproduces aberrations of an eye of an individual, wherein the computational model eye comprises a lens-supporting surface having the corneal topography of the eye of the individual and a model retina having a curvature of the human retina and a model fovea comprising a lattice of pixels that represent photoreceptors, wherein the distance between the model fovea and the center of the lens-supporting surface is equal to the visual axial length of the human eye, an optical design module for designing an optical model lens to compensate for the wavefront aberrations of the eye of the individual and to accommodate the corneal topography of the eye of the individual, a lens-designing optimization module for performing an iterative optimization process comprising the steps of (i) determining visual performance information of the optical model lens with the computational model eye, (ii) modifying the design of the optical model lens on the basis of said visual performance information to improve corrections of the aberrations of the eye, and (iii) repeating steps (i) and (ii) until visual performance of a modified design of the optical model lens is optimized, a mechanical design module for generating a CAD output file containing parameters for making said ophthalmic lens, based on an optimized optical model lens, a signal module for converting said CAD output file into control signals that control the computer-controllable manufacturing device to produce said ophthalmic lens, and a manufacturing control module for controlling the computer-controllable manufacturing device to produce said ophthalmic lens.

Preferably, the system for fabricating a customized ophthalmic lens further comprises a sensor system, which can determine the aberrations of the eye and the corneal topography of the eye under control of a computer system. More preferably, the system for fabricating a customized ophthalmic lens further comprises an optical metrology system for characterizing the fabricated ophthalmic lens.

FIG. 1 is the schematic representation of a system for designing and producing a customized ophthalmic lens according to a preferred embodiment of the present invention. The system of the present invention 100 includes a sensor system 110 that measures a set of characteristic data of an eye 12 of an individual including at least wavefront aberrations, corneal topography, and visual axial length. The set of characteristic data of the eye 12 are provided to a computer 120. The computer 120 designs a computational model eye on the basis of the set of characteristic data and an optical model lens to compensate for aberrations of the eye 12. The visual performance of the optical model lens is evaluated by the computer 120 with a computational model eye as shown in FIG. 3 or FIG. 4. The computer 120 redesigns an optimized optical model lens which is served as the basis for designing an ophthalmic lens 14 and generates a CAD output file containing parameters of the ophthalmic lens 14. The computer 120 then converts the CAD output file into control signals for a lathe 134, which then cuts the ophthalmic lens 14 or an insert for a mold for the ophthalmic lens 14 that would correct any aberrations of the eye 12. One example of a suitable lathe 134 would be a two-axis lathe with a 45o piezo cutter.

Figure 5:
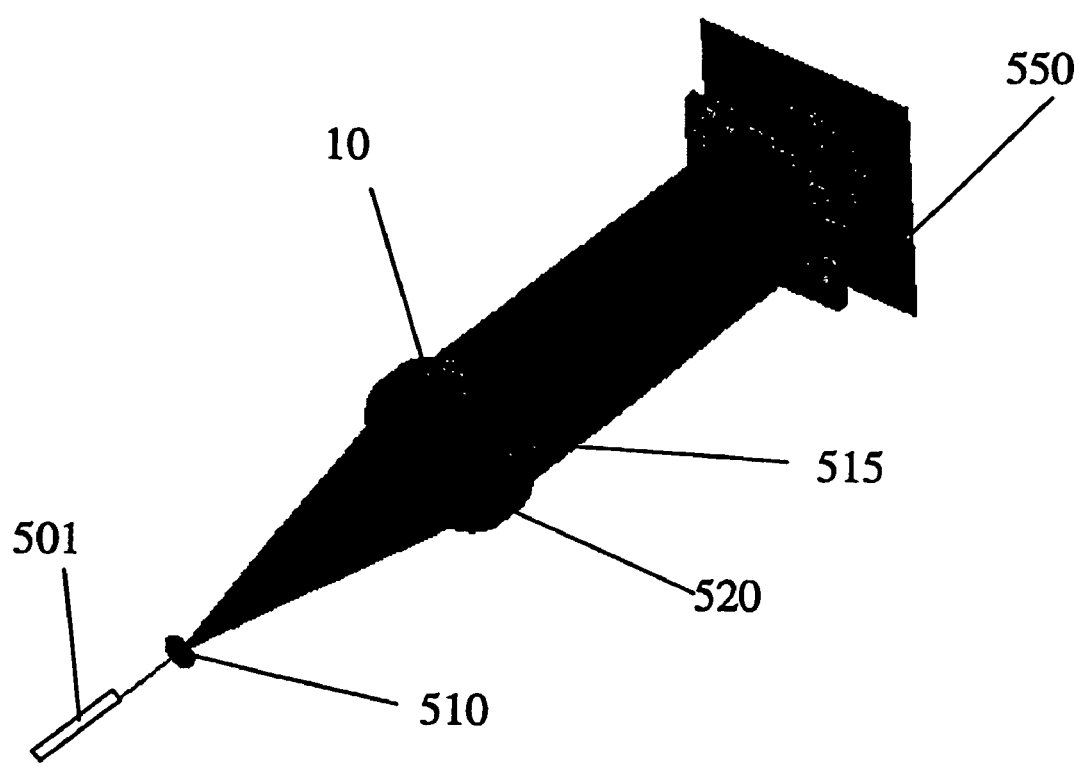

Once the lens 14 is cut by the lathe 134, the optical properties of the lens 12 are measured by an optical metrology system 138, as shown in FIG. 5, that generates metrology data of the lens 14, this metrology data is compared to a digital model of the optimized optical model lens to determine deviation of the actual lens 14 from the optimized optical model lens. The computer 120 calculates necessary corrections to the control signals to the lathe 134 and a new lens 14 is cut. This process continues in a closed loop until the actual lens 14 matches the optimal optical model lens within a suitable tolerance.

Figure 2:
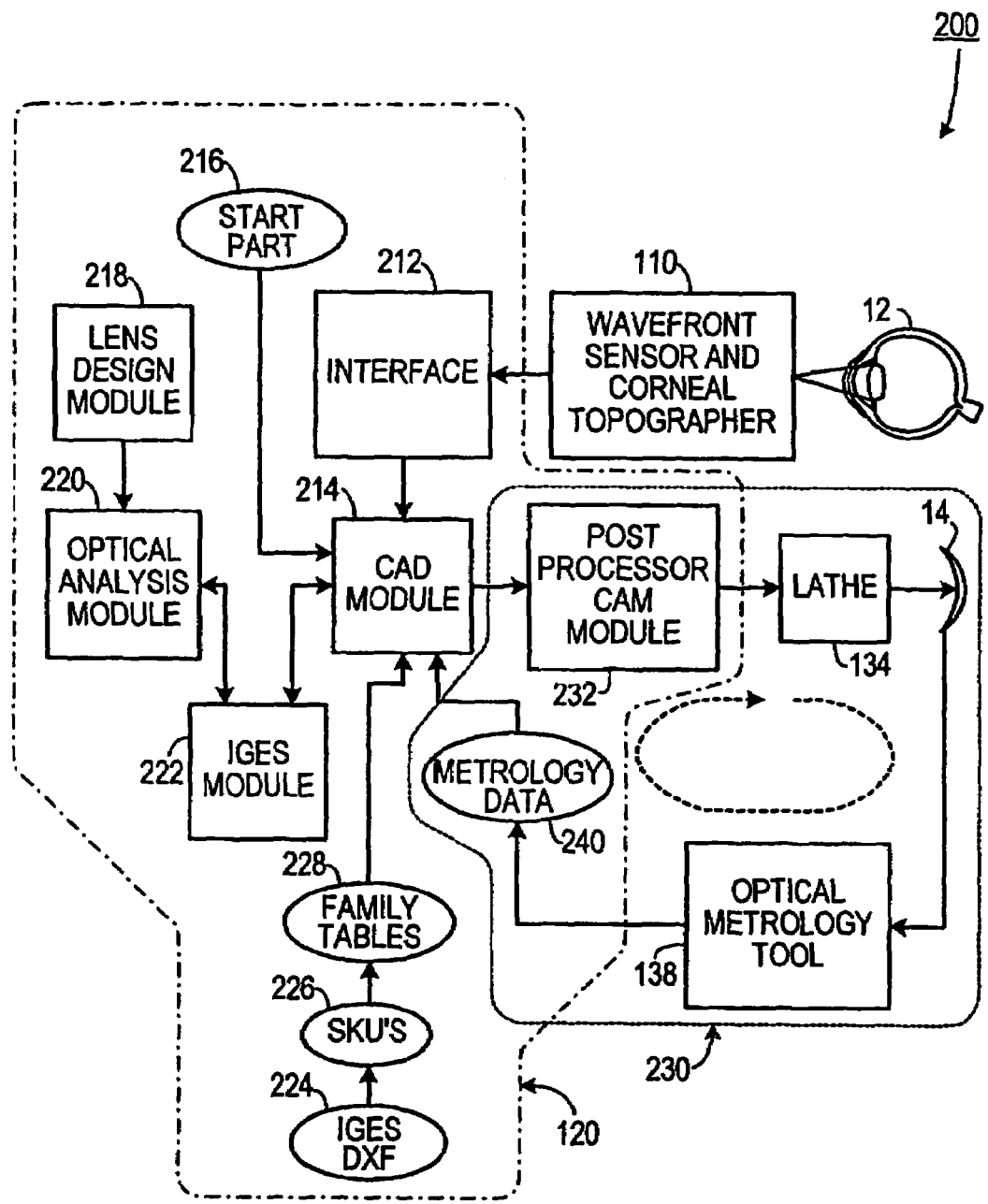

The process is shown in greater detail in FIG. 2. The wavefront sensor 110 measures the optical properties of the eye 12 and generates data that is transmitted to an interface 212, that is a resident program in the computer 120. The interface 212 generates a higher order polynomial function that describes the set of characteristic data of the eye 12. This information is fed into an optical computer aided design (CAD) module 218. One suitable example of an optical CAD design module is ASAP with the input from ZEMAX.

The lens design module 218 is used to design an optical model lens the visual performance of which is evaluated by an optical analysis module 220 comprising a computational model eye (FIG. 3 or FIG. 4) generated on the basis of the set of characteristic data of the eye 12. The result of visual performance is fed back to the optical CAD design module 218 to redesign an optimized optical model lens. The optical analysis module 220 is capable of performing ray tracing functions that incorporate a higher order polynomial description of the model lens. An IGES (International Graphics Exchange System) translating module 222 translates the resultant data from the optical analysis module 220 into a format that may be used by a mechanical CAD module 214. One suitable example of a mechanical CAD module 214 is PRO/ENGINEER.

The mechanical CAD module 214 also receives data from a start part 216 and/or from a set of family tables 228 that provide data relative to such parameters as: shrinkage, base curves, center thickness and power range. Stock keeping unit (SKU) data 226 provides the mechanical CAD module 214 with data that describes the type of lens being made and IGES/DXF data 224 provides information regarding the drawing format for the model lens.

The mechanical CAD module 214 generates design data, which is sent to a post processor and Computer Aided Manufacturing (CAM) module 232. The CAM module 232 generates the signals that control the lathe 134. The lens 14 is made by the lathe 134 and is analyzed by the metrology system 138, which generates metrology data 240 that the mechanical CAD module 214 uses in subsequent iterations of the design process.

Figure 6A:
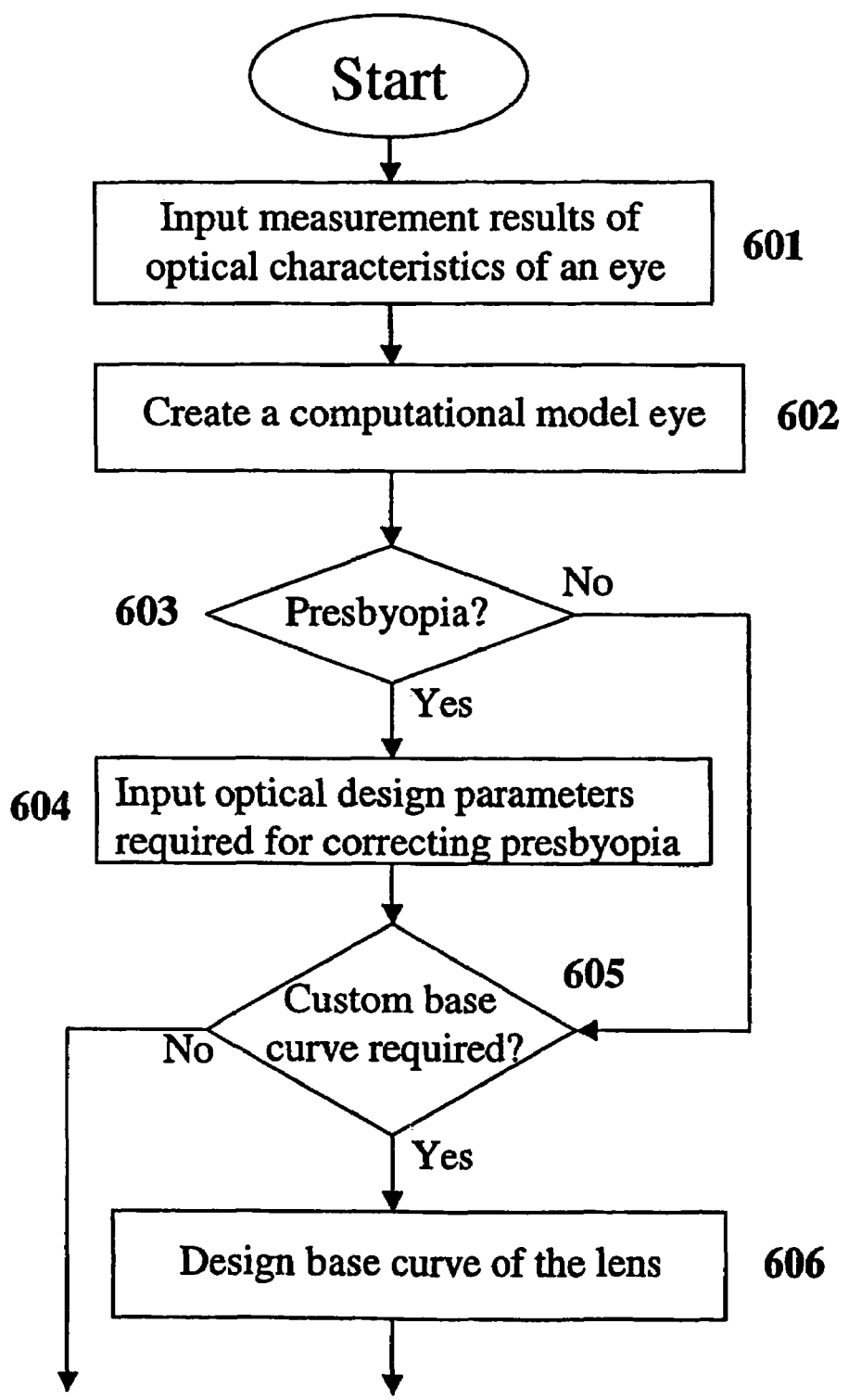
FIGS. 6A to 6C show a flow diagram depicting a process for designing and manufacturing ophthalmic lenses capable of correcting high order aberrations according to a preferred embodiment of the present invention.
Figure 6B:
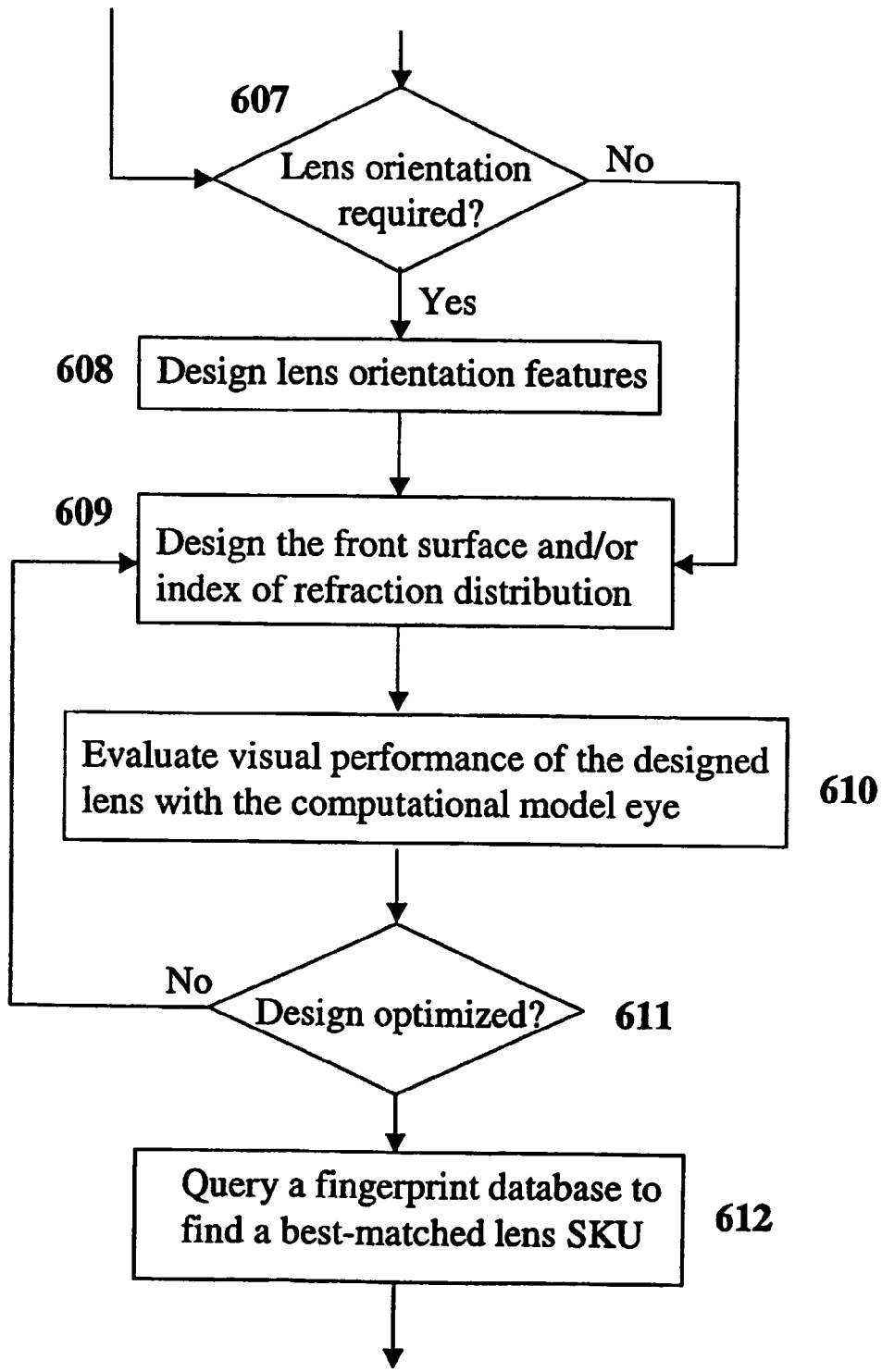
Figure 6C:
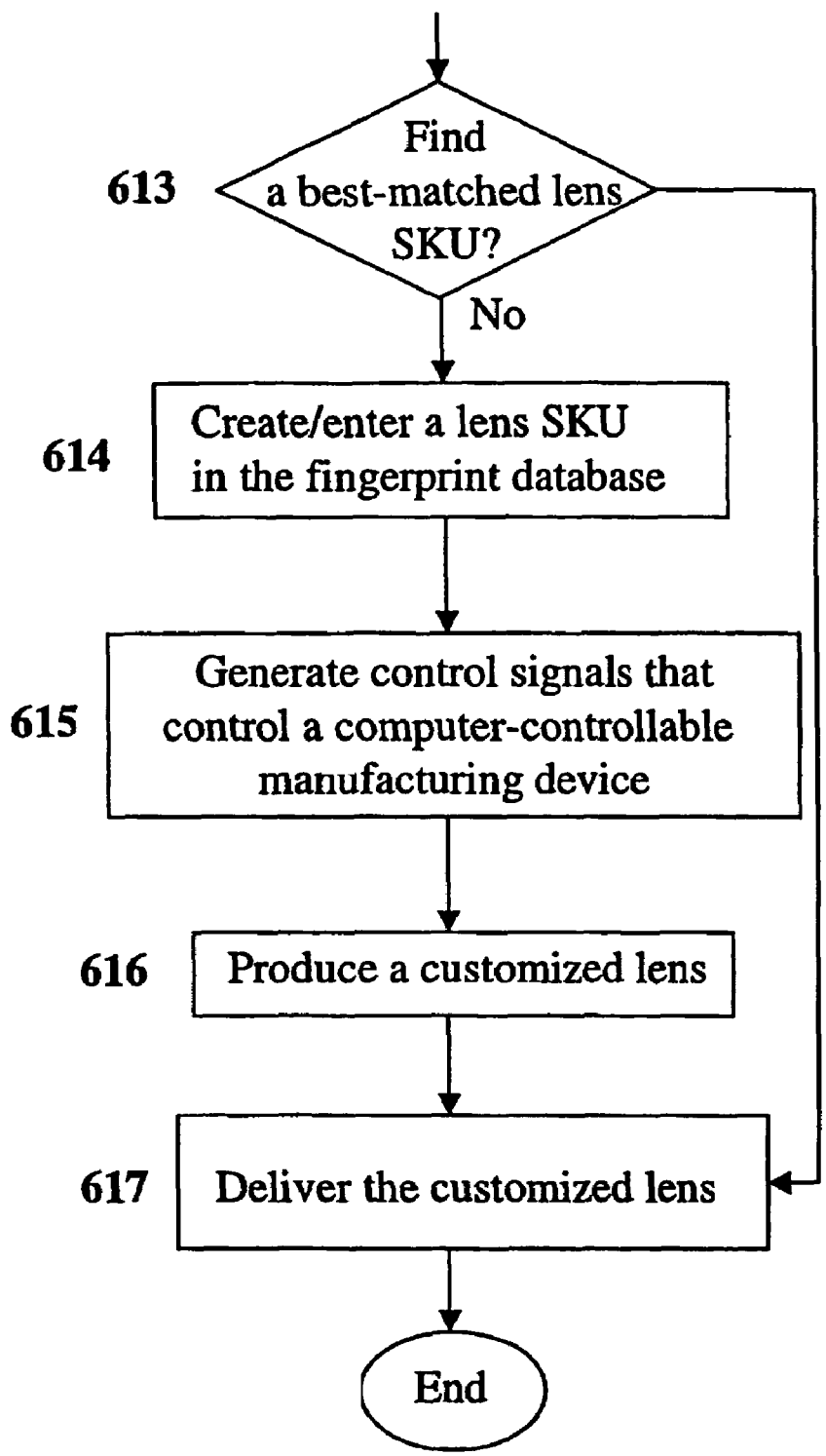

FIGS. 6A to 6C show a flow diagram of a process to produce a customized ophthalmic lenses according to a preferred embodiment of the invention. In step 601, a set of characteristic data of an eye of a patient is provided to a computer system. The set of characteristic data including wavefront aberrations and corneal topography data is served as the basis for creating a computational model eye in step 602. In step 603, if there is a need for correcting presbyopia, the computer system continues at step 604, else the computer system goes to step 605. In step 604, the optical design parameters, such as pupil diameter range, alternating/simultaneous function, monocular/binocular function, segment design (such as shape and number of zones, discrete/progressive zones, lens added power, etc.), and ages and occupational factors of that individual, are provided to the computer system or retrieved from a database. In step 605, if a special shape of the posterior surface of the customized contact lens is required, the computer system continues at step 606, else the computer system goes to step 607. In step 606, a special shape of the posterior surface of the customized contact lens is designed. In step 607, if the customized contact lens needs orientation features required for astigmatism, the computer system continues at step 608, else the computer system goes to step 609. In step 608, the orientation features are designed by the computer system. Any known, suitable orientation features can be used. Exemplary orientation features include, but are not limited to, a prism ballast or the like that uses a varying thickness profile to control the lens orientation, a faceted surface in which parts of the lens geometry are removed to control the lens orientation, a ridge feature which orients the lens by interacting with the eyelid. In step 609, an anterior surface is designed and the visual performance of the designed lens is evaluated in step 610 with the computational model eye generated in step 602. In step 611, if the visual performance of the designed lens is optimized, the computer system continues at step 612, else the computer system goes back to step 609 where the lens design is modified. In step 612, the computer system queries a database that contains a plurality of SKUs of customized contact lens. In step 613, if a best-match is located, the customized contact lens can be delivered, else the computer system continues at step 614, where a new lens SKU is created and entered in the database. In step 615, the computer system converts the optical design into a mechanical design and then generates control signals that control a computer-controllable manufacturing device to produce the customized contact lens in step 616.

Another preferred embodiment of the invention is an optical metrology system for characterizing an ophthalmic lens. FIG. 5 is a schematic representation of an optical metrology system according to a preferred embodiment of the present invention. The optical metrology system 138 of the present invention comprises a monochromatic point light source 501 and an aperture 510 which is served as a simulated fovea. The monochromatic light from the light source 501 passes through the aperture 510 and illuminates onto a diffraction limited model eye 520. In an alternative preferred embodiment, the model eye 520 can be a refractive optics (1) having a power of refraction equal to the overall power of refraction of the human eye or of an eye of an individual, or (2) having a power of refraction of the human cornea or of a cornea of an individual, depending on whether a contact lens or an intraocular lens (IOL) is under test. The front surface of the model eye 520 has a typical topography of the human cornea or a topography for accommodating a specific corneal topography of an individual. A contact lens 10 is mounted on the model eye 520 and lubricated by a lubricating system 515 which generates a simulated tear film between the contact lens 10 and the model eye 520. The contact lens 10 generates wavefront aberrations which are measured by a wavefront sensor 550. The simulated fovea 510 is capable of moving along the light path via manual means or via a precision motion control system to null defocus. An IOL can be placed between the model eye and the model fovea and its exact position is defined by an optical axial distance of 7.68 mm from the posterior surface of the IOL to the aperture 510.

The monochromatic point light source 501 preferably is a laser. By placing the simulated fovea 510 at the focal point, the metrology system of the present invention is capable of determining wavefront aberrations caused by the ophthalmic lens mounted on the diffraction limited model eye. Any discrepancy between the wavefront aberrations of an eye of an individual and the wavefront aberrations of the ophthalmic lens under metrology test will point out errors in the production of the ophthalmic lens and can provide instructions how to adjust control signals that control the cutting lathe. One of the unique features of the metrology system of the present invention is its capability to characterize a specific area of the lens by focusing the detection of the wavefront sensor in that area.

Preferably, the optical metrology system further comprises a pupil with adjustable size that is located between the model eye and the wavefront sensor.

More preferably, the optical metrology system further comprises a micro-electro-mechanical device (MEM) that can be controlled by a computer system so that the combination of the model eye and MEM reproduces the wavefront aberrations of an eye of an individual. The MEM is located in the optical pathway of the metrology system between the wavefront sensor and the model eye. When an ophthalmic lens is installed in such optical metrology system, any residual aberrations are reflective of the quality of the ophthalmic lens. Any known, suitable MEMs can be used in the invention. One example of MEMs is a programmable mirror array.

Another preferred embodiment of the invention is a method for characterizing the optical metrology of an ophthalmic lens, comprising the steps of:

(1) determining first wavefront aberrations before the ophthalmic lens is installed in an optical metrology system which comprises:

(a) a monochromatic point light source;

(b) a diffraction limited model eye in front of said light source, wherein said model eye has a posterior surface and an opposite anterior surface having an averaged corneal topography of a population;

(c) a lubricating system to simulate a tear film on the anterior surface of the model eye;

(d) an aperture which simulates the human fovea and is located between said light source and said model eye, wherein said simulated fovea is capable of moving along the light path via manual means or via a precision motion control system to null defocus; and (e) a wavefront sensor in front of said model eye;

(2) installing said ophthalmic lens in the optical metrology system;

(3) determining second wavefront aberrations derived from the optical metrology system having the ophthalmic lens emplaced therein; and (4) obtaining third wavefront aberrations by subtracting the first wavefront aberrations from the second wavefront aberrations, wherein the third wavefront aberrations are contributed by the ophthalmic lens.

Any ophthalmic lens which passes the optical metrology test should have wavefront aberrations that compensate for the wavefront aberrations of the eye of an idividual to the extent according to its optical design.

The ophthalmic lens can be a contact lens or an intraocular lens. Where the ophthalmic lens is a contact lens, the contact lens is mounted on the model eye which has a power of refraction equal to an averaged power of refraction of eyes of a population and there is a tear film between the posterior surface of the contact lens and the anterior surface of the model eye.

Where the ophthalmic lens is a phakic intraocular lens, the phakic intraocular lens is mounted on the model eye which has a power of refraction equal to an averaged power of refraction of eyes of a population and the phakic intraocular lens is placed at a position between the model eye and the aperture.

Where the ophthalmic lens is an aphakic intraocular lens, the model eye is a model cornea having a power of refraction equal to an averaged power of refraction of corneas of a population and the intraocular lens is placed at a position between the model eye and the aperture. Preferably, the distance from the posterior surface of the aphakic intraocular lens to the aperture is equal to 7.68 mm.

In another preferred embodiment, the present invention provides a method for characterizing the optical metrology of an ophthalmic lens, comprising the steps of:

(1) determining first wavefront aberrations before installing said ophthalmic lens in an optical metrology system which comprises:

(a) a monochromatic point light source;

(b) a diffraction limited model eye in front of said monochromatic point light source, wherein said model eye has an anterior surface having a typical topography of the human cornea or a topography for accommodating a specific corneal topography of an eye of an individual;

(c) a lubricating system to simulate a tear film on the model eye;

(d) a simulated fovea which is located between said light source and said model eye, wherein said simulated fovea is capable of moving along the light path via manual means or via a precision motion control system to null defocus;

(e) a wavefront sensor in front of said model eye, wherein said wavefront sensor is capable of measuring wavefront aberrations caused by said contact lens; and (f) a computer-controllable MEM which is located between the model eye and the wavefront sensor, wherein the computer-controllable MEM generates desired wavefront aberrations of the eye which needs to be corrected;

(2) installing the ophthalmic lens in the optical metrology system; and (3) determining second wavefront aberrations derived from the optical metrology system having the ophthalmic lens emplaced therein; and (4) obtaining third wavefront aberrations by subtracting the first wavefront aberrations from the second wavefront aberrations, wherein the third wavefront aberrations are uncorrectable wavefront aberrations of the eye with the ophthalmic lens or additional undesired aberrations contributed by the ophthalmic lens.

The above lens-designing and fabricating methods and systems and the metrology method and system of the present invention can find use in manufacturing customized ophthalmic lenses. The method for manufacturing customized ophthalmic lenses comprises the steps of:

(1) analyzing eyes of each of individuals from a population to obtain a set of characteristic data comprising aberrations and corneal topography;

(2) compiling population statistics of aberrations and corneal topographies;

(3) creating a plurality of computational model eyes each representing one of a plurality of nominal segments of the population, based on an averaged aberrations and an averaged cornea topography for this nominal segment of the population;

(4) designing a plurality of optical model lenses each of which accommodates the averaged corneal topography of one of the plurality of nominal segment of the population and corrects the averaged aberrations of the corresponding nominal segment of the population;

(5) optimizing designs of the plurality of the optical model lenses with one of the plurality of the computational model eyes;

(6) transforming the plurality of the optimized optical model lenses into a plurality sets of mechanical parameters each for making one contact lens;

(7) creating one stock keeping unit (SKU) for each of each of the contact lenses; and (8) manufacturing said ophthalmic lenses having a specific SKU.

A SKU can contain information for identifying a specific ophthalmic lens and for manufacturing this specific ophthalmic lens. Preferably, a SKU comprises wavefront aberrations and a corneal topography representing a nominal segment of a population. The wavefront aberrations and the corneal topography can be quantified in any forms, preferably in weighted polynomials. More preferably, the wavefront aberrations and the corneal topography are quantified in one identical form. Much more preferably, the wavefront aberrations and the corneal topography are quantified in Zernike polynomials plus spline-based mathematical functions. The Zernike polynomials can have at least second order modes, preferably at least third order modes, and more preferably at least fifth order modes. More preferably, a SKU further comprises at least a member selected from the group consisting of lens material, shrinkage, non-optical edge zone and its curvature, center thickness, bevel, lenticular, and edge.

Together with a communication network, such as the Internet, the above methods and systems for designing/fabricating a customized ophthalmic lens and for manufacturing customized ophthalmic lenses are conducive to conducting electronic business involving ordering and delivering of customized lenses.

The Internet comprises a vast number of computers and computer networks that are interconnected through communication links. The interconnected computers exchange information using various services, such as electronic mail, Gopher, and the World Wide Web ("WWW"). The WWW service allows a server computer system (i.e., Web server or Web site) to send graphical Web pages of information to a remote client computer system. The remote client computer system can then display the Web pages. Each resource (e.g., computer or Web page) of the WWW is uniquely identifiable by a Uniform Resource Locator ("URL"). To view a specific Web page, a client computer system specifies the URL for that Web page in a request (e.g., a HyperText Transfer Protocol ("HTTP") request). The request is forwarded to the Web server that supports that Web page. When that Web server receives the request, it sends that Web page to the client computer system. When the client computer system receives that Web page, it typically displays the Web page using a browser. A browser is a special-purpose application program that effects the requesting of Web pages and the displaying of Web pages.

Currently, Web pages are typically defined using HyperText Markup Language ("HTML"). HTML provides a standard set of tags that define how a Web page is to be displayed. When a user indicates to the browser to display a Web page, the browser sends a request to the server computer system to transfer to the client computer system an HTML document that defines the Web page. When the requested HTML document is received by the client computer system, the browser displays the Web page as defined by the HTML document. The HTML document contains various tags that control the displaying of text, graphics, controls, and other features. The HTML document may contain URLs of other Web pages available on that server computer system or other server computer systems.

Figure 7:
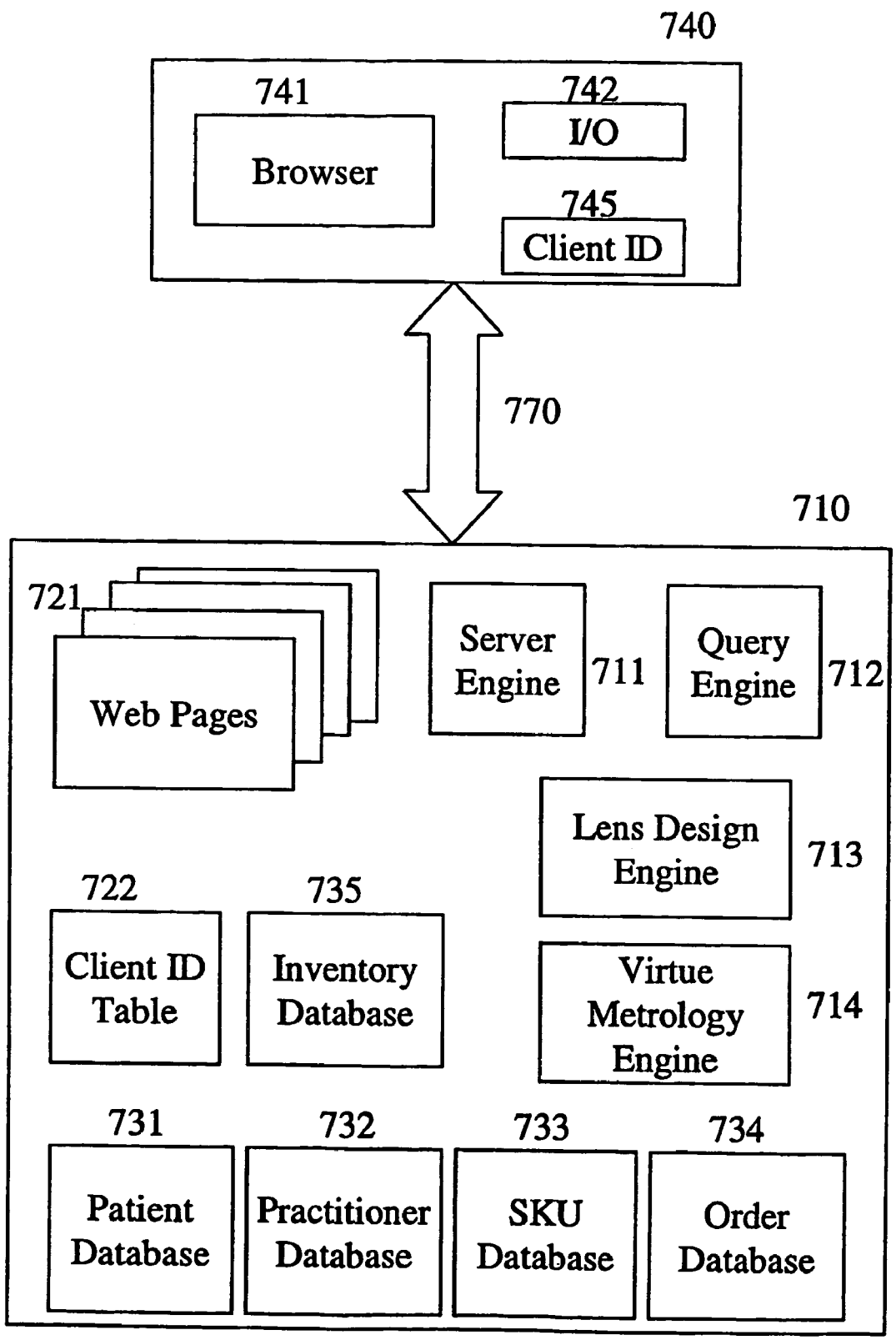
FIG. 7 is block diagram schematically depicting a system and method for placing an order for purchasing a pair of customized ophthalmic lenses according to a preferred embodiment of the invention.

FIG. 7 is a block diagram illustrating a preferred embodiment of the invention. This preferred embodiment provides a method for placing an order of a customized ophthalmic lens over the Internet using the World Wide Web.

Referring to FIG. 7, a server system 710 comprises a server engine 711, a lens design engine 713, a query engine 712, a metrology engine 714 (optional), a client identifier table 722, various Web pages 721, a patient database 731, an eye-care practitioner database 732, an SKU database 733, an order database 734, and an inventory database 735.

The server engine 711 receives HTTP requests to access Web pages identified by URLs and provides the Web pages to the various client systems. The server engine also assigns and sends a client identifier to a client computer system once when the client computer system first interacts with the server system. From then on, the client computer system includes its client identifier with all messages sent to the server system so that the server system can identify the source of the message.

The lens design engine 713 is a computer program that implements the above-described method for designing a customized ophthalmic lens. The lens design engine designs a pair of ophthalmic lenses on the basis of the wavefront aberrations and corneal topographies of the eyes of an individual and generates a set of physical and optical parameters for this pair of ophthalmic lenses optimized for accommodating the corneal topographies and for correcting aberrations. Such set of physical and optical parameters can be used to produce a new pair of customized lenses or be utilized by the query engine 712, that is a computer program, to search against a SKU database. The query engine employs an algorithm to find for each of the two eyes a list of SKUs each of which can adequately accommodate the corneal topography of that eye and adequately correct the aberrations of that eye. Such lists of SKUs with lens information, such as the conformity of each lens to the corneal topography of the corresponding eye and a reachable visual acuity with a specific SKU. Preferably, the conformity of each lens to the corneal topography of the corresponding eye is displayed in a client computer system as an interactive three-dimensional graphic representation and the reachable visual acuity with a specific SKU is displayed in the same computer system as a graphic representation, for example, a simulated retina image quality.

"A contact lens can correct adequately the aberrations of an eye", as used herein, means that the lens can correct the aberrations of the eye at least to the extent as prescribed by an eye-care practitioner.

The metrology engine 714 is a computer program that is able to characterize the optical metrology of an ophthalmic lens identified by a SKU identifier using the computer model eye created by the lens design engine 713. The metrology engine determines the visual performance of that ophthalmic lens and estimates the visual acuity of an eye with that ophthalmic lens.

The patient database 731 contains patient-specific order information, such as name of the patient, billing information, and shipping information, for various patients or potential patients.

The eye-care practitioner database 732 contains eye-care practitioner-specific order information, such as name of the patient under the eye-care practitioner's care, and address and contact information of the eye-care practitioner, for various patients or potential patients.

The SKU database 733 contains descriptions and identifiers of SKUs of various ophthalmic lenses that have been and can be produced.

The order database 734 contains an entry for each order that has not yet been shipped to a patient or an eye-care practitioner.

The inventory database 735 contains SKU identifiers of ophthalmic lenses that are currently in stock.

The client identifier table 722 contains a mapping from each client identifier, which is a globally unique identifier that uniquely identifies a client computer system, to the patient or eye-care practitioner last associated with that client computer system.

The client computer system 740 comprises a browser 741, an assigned client identifier 745, and input/output (I/O) interface devices 742. The client identifier is stored in a file, referred to as a "cookie." An input device receives input (such as data, commands, etc.) from human operators and forwards such input to the client computer system 740 via a communication medium. Any known, suitable input device may be used in the present invention, such as a keyboard, pointing device (mouse, roller ball, track ball, light pen, etc.), touch screen, etc. User input may also be stored and then retrieved, as appropriate, from data/command files. An output device outputs information to human operators. The client computer system transfers such information to the output device via a communication medium. Any well known, suitable output device may be used in the present invention, such as a monitor, a printer, a floppy disk drive, a text-to-speech synthesizer, etc. In a more preferred embodiment, a sensor system, that can measure at least wavefront aberrations, preferably at least wavefront aberrations and corneal topography of the eyes of an individual, is connected to the client computer system via a communication medium.

The client computer system may comprise any combination of hardware and software that can interact with the server system. One example is a client computer system comprising a television-based system.

It will be understood that the method of the invention for ordering a pair of customized lenses can be implemented in various environments other than the Internet. Exemplary environments other than the Internet include, but are not limited to, an electronic mail environment, local area network, wide area network, and point-to-point dial up connection.

There are some advantages associated with the lens-ordering system and method of the invention. One advantage is that measurements of the vision conditions of the eyes of a patient can be fast and accurate. Another advantage is that a patient will have the choice to select a pair of ophthalmic lenses that gives him a desired visual acuity and wearer's comfort. With the lens-ordering system and method of the invention, it may be possible to set up an eye examination/order station in a public area, such as a shopping mall. Patients can have their eyes examined and order pairs of ophthalmic lenses.

Another preferred embodiment of the invention is a system for examining the eyes of an individual and ordering a pair of customized contact lenses, the system comprising:

(1) a sensor system that determines a set of characteristic data comprising wavefront aberrations and corneal topography data of a first and a second eye of the patient, wherein the sensor system is connected through a communication media to a client computer system;

(2) the client computer system comprising:

(i) a customer identifier that identifies the client computer system a patient and/or an eye-care practitioner is using to connect to a server system;

(ii) a sending/receiving means for: (a) sending a first request to the server system to look for a pair of contact lenses capable of correcting the aberrations of both eyes, the first request including the set of characteristic data of the first and second eyes so that the server system can compile and supply lens information related to a first list and a second list of SKUs, wherein each of the first list of SKUs has a posterior surface adequately accommodating the corneal topography of the first eye and can correct adequately the aberrations of the first eye, and wherein each of the second list of SKUs has a posterior surface adequately accommodating the corneal topography of the second eye and can correct adequately the aberrations of the second eye; and (b) receiving the lens information;

(iii) a displaying means for displaying lens information that helps a patient to select a pair of customized lenses; and (iv) a selecting means for selecting a pair of SKUs identified by a first SKU identifier and a second SKU identifier or a new pair of customized contact lenses and for sending a second request to the server system to order the pair of SKUs or the new pair of customized contact lenses to be made, along with the customer identifier so that the server system can locate additional information to complete and fulfill the order.

Preferably, sets of characteristic data of eyes further comprise visual axial length. More preferably, sets of characteristic data of eyes are determined at various pupil sizes.

Preferably, lens information comprises the conformity of each lens to the corneal topography of the corresponding eye and a reachable visual acuity with a specific SKU. The conformity of each lens to the corneal topography of the corresponding eye preferably is displayed in a client computer system as an interactive three-dimensional graphic representation. The reachable visual acuity with a specific SKU preferably is displayed in the same computer system as a graphic representation, more preferably a graphics representing a simulated retina image quality.

The invention claimed is:

1. A method for designing a customized ophthalmic lens, the method comprising the steps of:
   (1) providing a set of characteristic data of an eye of an individual, wherein said set of characteristic data comprises wavefront aberrations of the eye and corneal topography;
   (2) creating a computational model eye that reproduces the wavefront aberrations of the eye of the individual, wherein the computational model eye comprises a lens-supporting surface having the corneal topography of the eye of the individual and a model retina having a model fovea comprising a lattice of pixels that represent photoreceptors and can be used to perform bitmap image analysis and/or ghost image analysis of an optical model lens to be evaluated, wherein the distance between the model fovea and the center of the lens-supporting surface is equal to a visual axial length of the human eye;
   (3) designing an optical model lens which is capable of compensating for the wavefront aberrations of the eye, wherein said optical model lens has an anterior surface and an opposite posterior surface;
   (4) evaluating the visual performance of said optical model lens with the computational model eye;
   (5) obtaining visual performance information of said optical model lens;
   (6) modifying the design of said optical model lens on the basis of said visual performance information to improve corrections of the aberrations of the eye, if the visual performance of said optical model lens is not optimal;
   (7) repeating steps (4) to (6), if necessary, until the visual performance of said optical model lens is optimal; and
   (8) transforming the optimized optical model lens into a set of mechanical parameters for making said customized ophthalmic lens.

2. A method of claim 1, wherein the customized ophthalmic lens is a contact lens.

3. A method of claim 2, wherein the computational model eye is:

(1) a reduced computational model eye that comprises an optical refractive element having a first optical surface and an opposite second optical surface and the model retina, wherein the first optical surface is the lens supporting surface; or (2) an anatomical computational model eye that comprises a model cornea having an anterior surface and an opposite posterior surface, a model crystalline lens, and the model retina, wherein the anterior surface of the model cornea is the lens-supporting surface, wherein the model cornea, the model crystalline lens and the model retina are arranged in a way identical to the arrangement of their corresponding optical elements in the human eye.

4. A method of claim 1, wherein the customized ophthalmic lens is an intraocular lens.

5. A method of claim 3, wherein the computational model eye is an anatomical computational model eye that comprises a model cornea having an anterior surface and an opposite posterior surface, a model crystalline lens, and the model retina, wherein the anterior surface of the model cornea is the lens-supporting surface, wherein the model cornea, the model crystalline lens and the model retina are arranged in a way identical to the arrangement of their corresponding optical elements in the human eye.

6. A method for designing a customized ophthalmic lens, comprising the steps of:

(1) providing a set of characteristic data of an eye of an individual, wherein said set of characteristic data comprises wavefront aberrations of the eye and corneal topography;

(2) creating a computational model eye that reproduces the wavefront aberrations of the eye of the individual, wherein the computational model eye comprises a lens-supporting surface having the corneal topography of the eye of the individual and a model retina having a model fovea comprising a lattice of pixels that represent photoreceptors, wherein the distance between the model fovea and the center of the lens-supporting surface is equal to a visual axial length of the human eye, wherein the computational model eye is (a) a reduced computational model eye that comprises an optical refractive element having a first optical surface and an opposite second optical surface and the model retina, wherein the first optical surface is the lens supporting surface, or (b) an anatomical computational model eye that comprises a model cornea having an anterior surface and an opposite posterior surface, a model crystalline lens, and the model retina, wherein the anterior surface of the model cornea is the lens-supporting surface, wherein the model cornea, the model crystalline lens and the model retina are arranged in a way identical to the arrangement of their corresponding optical elements in the human eye, wherein the computational model eye further comprises a model pupil which is located between the optical refractive element and the model retina in the reduced computational model eye or between the model cornea and the model crystalline lens in the anatomical model eye, wherein the size of the model pupil is about from 2.0 mm to 8.0 mm and adjustable according to the individual's age and/or illumination light intensity;

(3) designing an optical model lens which is capable of compensating for the wavefront aberrations of the eye, wherein said optical model lens has an anterior surface and an opposite posterior surface;

(4) evaluating the visual performance of said optical model lens with the computational model eye;

(5) obtaining visual performance information of said optical model lens;

(6) modifying the design of said optical model lens on the basis of said visual performance information to improve corrections of the aberrations of the eye, if the visual performance of said optical model lens is not optimal;

(7) repeating steps (4) to (6), if necessary, until the visual performance of said optical model lens is optimal; and (8) transforming the optimized optical model lens into a set of mechanical parameters for making said customized ophthalmic lens.

7. A method of any one of claim 6, wherein the size of the fovea is about 2 mm.

8. A method of any one of claim 7, wherein the lattice of pixels is a hexagonal lattice of pixels with a diameter of about 2.5 micron.

9. A method of claim 8, wherein the posterior surface of said optical model lens accommodates the corneal topography of the eye of the individual.

10. A method of claim 9, wherein each of the anterior surface and posterior surface of the optical model lens is quantified by a mathematical description.

11. A method of claim 10, wherein the mathematical description comprises one ore more mathematical functions selected from the group consisting of conic functions, quadric functions, polynomials of any degree, Zernike polynomials, exponential functions, trigonometric functions, hyperbolic functions, rational functions, Fourier series, and wavelets.

12. A method of claim 11, wherein the mathematical description comprises Zernike polynomials.

13. A method of claim 12, wherein the mathematical description further comprises spline-based mathematical functions.

14. A method of claim 9, wherein the visual performance information comprises one or more members selected from the group consisting of wavefront aberrations, point spread function (PSF), line spread function (LSF), modulation transfer function (MTF), phase transfer function, contrast threshold function, contrast sensitivity function (CFS), bitmap image analysis, ghost image analysis, focal length analysis, and optical power analysis.

15. A method of claim 14, wherein the optical design of said optical model lens is optimized by using a set of aberration coefficients that represent the wavefront aberrations of the eye of the individual as weighted operands in an optical design optimization loop, on the basis of the visual performance information obtained in step 5.

16. A method of claim 14, wherein the optical design of said optical model lens is optimized by using artificial intelligence (AI) programs or neural networks, on the basis of the visual performance information obtained in step 5.

17. A method of claim 16, wherein the step of transforming the optimized optical model lens into a set of mechanical parameters for making said customized ophthalmic lens is performed by translating the design of the optimized optical model lens back and forth between an optical CAD system and a mechanical CAD system using a translation format which allows a receiving system, either optical CAD or mechanical CAD, to construct NURBs or Beizier surfaces of an intended design.

18. A method of claim 8, wherein the posterior surface of said optical model lens accommodates an averaged corneal topography derived from population studies.

19. A method of claim 6, further comprising the steps of:
(9) converting the set of mechanical parameters for making the lens into control signals that control a computer-controllable manufacturing device; and
(10) producing the lens using the computer controllable manufacturing device.

20. A method of claim 19, wherein the computer controllable manufacturing device is a computer-controllable lathe.

21. A method for creating a computational model eye, the method comprising the steps of:
(1) providing a set of characteristic data of an eye of an individual, wherein said set of characteristic data comprises wavefront aberrations and corneal topography data of the eye of the individual;
(2) converting the corneal topography data into a mathematical description representing a first surface of a first refractive optical element, the first optical refractive element having the first surface and an opposite second surface;
(3) designing and optimizing the second surface of the first refractive optical element so that the first refractive optical element, alone or in combination with a second refractive optical element that has a third surface and an opposite fourth surface and an index of refraction distribution, reproduces the wavefront aberrations of the eye;
(4) designing a model retina that has a curvature of the human retina and comprises a model fovea having a lattice of pixels representing photoreceptors; and
(5) arranging the first refractive optical element and the model retina along an optical axis in a way such that the distance between the fovea and the center of the first surface of the first refractive optical element is equal to the visual axial length of the human eye,
wherein the size of fovea is about 2 mm and wherein the lattice of pixels is a hexagonal lattice of pixels with a diameter of about 2.5 micron.

22. A method of claim 21, wherein each of the first surface and second surface of the first refractive optical element is quantified by a mathematical description.

23. A method of claim 22, wherein the mathematical description comprises one ore more mathematical functions selected from the group consisting of conic functions, quadric functions, polynomials of any degree, Zernike polynomials, exponential functions, trigonometric functions, hyperbolic functions, rational functions, Fourier series, and wavelets.

24. A method of claim 23, wherein the mathematical description comprises Zernike polynomials.

25. A method of claim 24, wherein the mathematical description further comprises spline-based mathematical functions.

26. A method of claim 25, wherein the computational model eye further comprises a model pupil which is located between the first refractive optical element and the model retina, wherein the size of the model pupil is about from 2.0 mm to 8.0 mm and adjustable according to the individual's age and/or illumination light intensity.

27. A method of claim 26, wherein the computational model eye comprises a model crystalline lens as the second refractive optical element and a model corneal as the first refractive optical element, wherein the model crystalline lens is constructed on the basis of the crystalline lens of the human eye so that the model crystalline lens has a power of refraction equal to the power of refraction of the human eye, wherein the model cornea, the model crystalline lens and the model retina are arranged in a way identical to the arrangement of their corresponding elements in the human eye.

28. A system for characterizing the optical metrology of an ophthalmic lens, the system comprising:
(a) a monochromatic point light source;
(b) a diffraction limited model eye in front of said monochromatic point light source, wherein said model eye has a posterior surface and an opposite anterior surface having an averaged corneal topography of a population;
(c) a lubricating system to simulate a tear film on the anterior surface of the model eye;
(d) an aperture which simulates the human fovea and is located between said light source and said model eye, wherein said simulated fovea is capable of moving along the light path via manual means or via a precision motion control system to null defocus;
(e) a wavefront sensor in front of said model eye; and
(f) a micro-electro-mechanical device (MEM) that is controlled by a computer system to generate desired wavefront aberrations of the eye which needs to be corrected, wherein the MEM is located in the optical pathway of the metrology system between the wavefront sensor and the model eye.

29. A system of claim 28, wherein the light source is a laser.

30. A system of claim 29, further comprising an additional aperture to simulate the pupil or iris of the eye, wherein the additional aperture is located along the optical pathway between the wavefront sensor and the refractive optics.

31. A system of claim 30, wherein the ophthalmic lens is a contact lens is mounted on the model eye but separated from the model eye by the tear film between the posterior surface of the contact lens and the anterior surface of the model eye, wherein the model eye has a power of refraction equal to an averaged power of refraction of eyes of a population.

32. A system of claim 30, wherein the ophthalmic lens is an intraocular lens is installed in a position that is between the aperture and the anterior surface of the model eye along the optical axis of the model eye, wherein the model eye has a power of refraction equal to an averaged power of refraction of corneas of a population.

33. A system of claim 32, wherein the MEM is deformable mirror.

34. A system of claim 30, wherein the MEM is deformable mirror.

35. A system of claim 34, further comprising a hardware or software means for limiting a region of the ophthalmic lens under test to a specific optical zone.

* * * * *